(12) United States Patent
Zilbershlag

(10) Patent No.: US 12,296,168 B2
(45) Date of Patent: May 13, 2025

(54) HIDDEN COCHLEAR IMPLANT SYSTEM

(71) Applicant: SMART SOUND LTD., Nirit (IL)

(72) Inventor: Harel Zilbershlag, Givat Shmuel (IL)

(73) Assignee: Smart Sound LTD., Nirit (IL)

( * ) Notice: Subject to any disclaimer, the term of this patent is extended or adjusted under 35 U.S.C. 154(b) by 769 days.

(21) Appl. No.: 17/339,380

(22) Filed: Jun. 4, 2021

(65) Prior Publication Data

US 2021/0290959 A1    Sep. 23, 2021

Related U.S. Application Data

(63) Continuation-in-part of application No. PCT/IB2019/060541, filed on Dec. 8, 2019.

(60) Provisional application No. 62/859,481, filed on Jun. 10, 2019, provisional application No. 62/809,663, filed on Feb. 24, 2019, provisional application No. 62/777,138, filed on Dec. 8, 2018.

(51) Int. Cl.
*A61N 1/36*      (2006.01)
*A61N 1/05*      (2006.01)
*H04R 25/00*   (2006.01)

(52) U.S. Cl.
CPC ....... *A61N 1/36038* (2017.08); *A61N 1/0541* (2013.01); *H04R 25/554* (2013.01)

(58) Field of Classification Search
CPC . A61N 1/36038; A61N 1/0541; H04R 25/554
See application file for complete search history.

(56) References Cited

U.S. PATENT DOCUMENTS

| | | | |
|---|---|---|---|
| 5,721,783 A * | 2/1998 | Anderson | H04M 1/72421 381/328 |
| 6,537,200 B2 | 3/2003 | Leysieffer et al. | |
| 8,218,803 B2 | 7/2012 | Fickweiler et al. | |
| 2004/0028251 A1* | 2/2004 | Kasztelan | H04R 25/554 381/322 |
| 2005/0033384 A1* | 2/2005 | Sacha | A61N 1/36038 607/57 |
| 2011/0144719 A1* | 6/2011 | Perkins | A61N 1/36038 607/57 |
| 2011/0144749 A1* | 6/2011 | Kim, I | A61N 1/36039 607/57 |
| 2014/0073262 A1 | 3/2014 | Gutierrez et al. | |

(Continued)

*Primary Examiner* — Lindsey G Wehrheim
(74) *Attorney, Agent, or Firm* — William H. Dippert; Laurence A. Greenberg; Werner H. Stemer

(57) ABSTRACT

A hidden cochlear implant system comprises a canal unit and an implanted unit. The canal unit comprises at least one canal microphone; a canal modulator; a canal transmitting antenna: and a canal electrical power source, wherein the at least one canal microphone is electrically connected to the canal modulator, the canal modulator is electrically connected to the canal transmitting antenna, and the canal electrical power source is electrically connected to any component of the canal unit that requires supply of electrical power. The implanted unit comprises a cochlear receiving antenna; a processor; and an electrode array, wherein the cochlear receiving antenna is electrically connected to the processor, and the processor is electrically connected to the electrode array. Additional embodiments of the hidden cochlear implant are disclosed herein.

22 Claims, 15 Drawing Sheets

(56) References Cited

U.S. PATENT DOCUMENTS

2014/0105434 A1* 4/2014 Goorevich .......... H04R 25/606
381/320

* cited by examiner

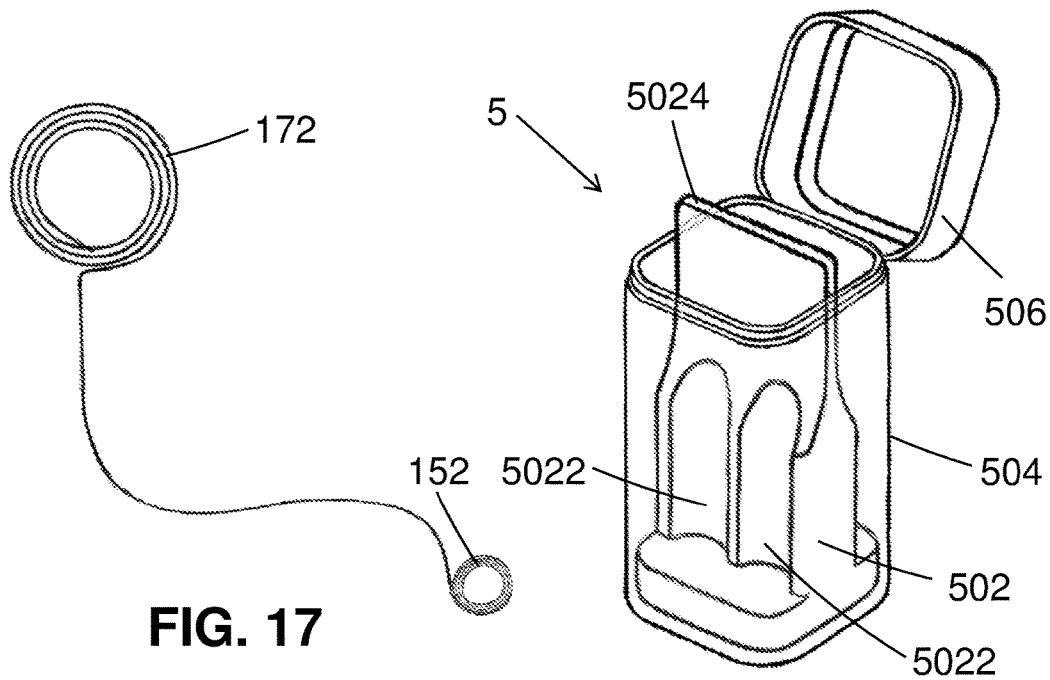
FIG. 17
FIG. 18
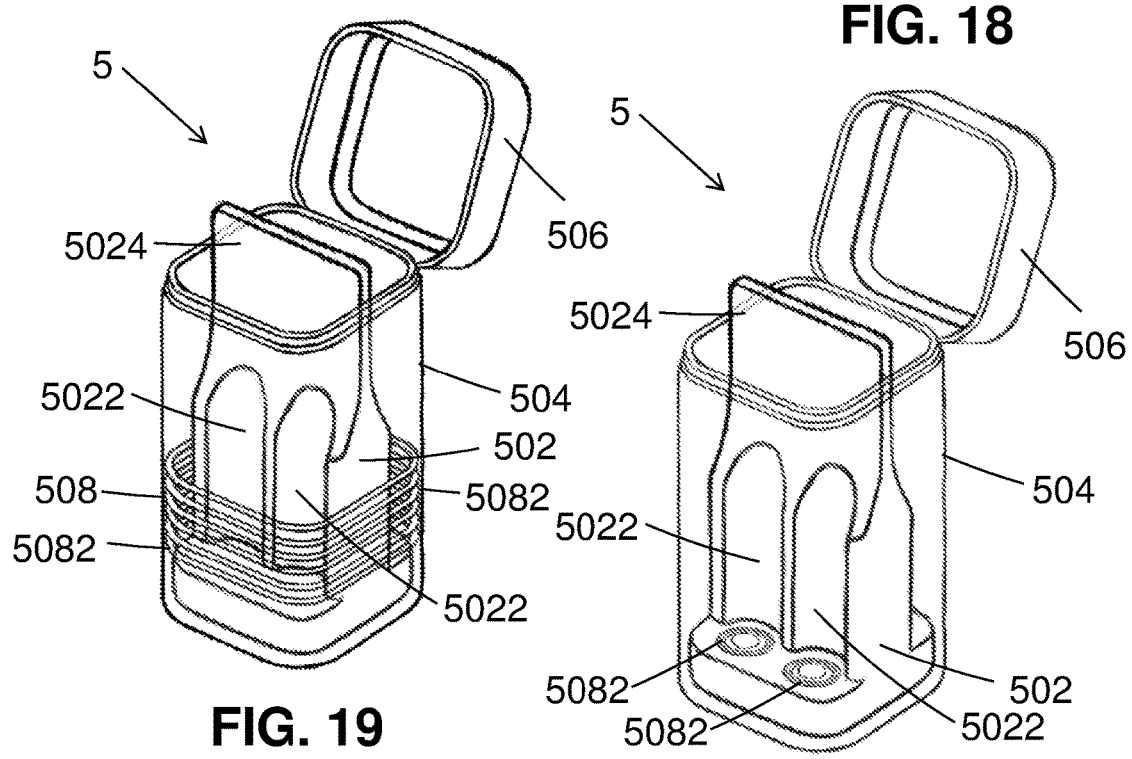
FIG. 19
FIG. 20

HIDDEN COCHLEAR IMPLANT SYSTEM

CROSS-REFERENCE TO RELATED APPLICATION

This application is a continuation-in-part of the U.S. National Phase entry of International Patent Application No. PCT/IB2019/060541, filed Dec. 8, 2019. This application claims priority to U.S. Provisional Patent Application Ser. No. 62/777,138, filed Dec. 8, 2018, U.S. Provisional Patent Application Ser. No. 62/809,663, filed Feb. 24, 2019, and U.S. Provisional Patent Application Ser. No. 62/859,481, filed Jun. 10, 2019, the entire contents of which is incorporated herein by reference in its entirety.

FIELD

The present subject matter relates to hearing aids. More particularly, the present subject matter relates to hearing aid of the cochlear implants.

BACKGROUND

A hearing aid is a device designed to improve hearing by making sound audible to a person with hearing loss. Among various types of hearing aids currently available, cochlear implants are of interest to the present subject matter.

A cochlear implant is a surgically implanted neuroprosthetic device configured to provide a person with moderate to profound sensorineural hearing loss a modified sense of sound. Cochlear implants bypass the normal acoustic hearing process to replace it with electric signals that directly stimulate the auditory nerve. A user of a cochlear implant can, after intensive auditory training, learn to interpret the signals stimulating the auditory nerve as sound and speech.

FIG. 1 schematically illustrates, according to an exemplary embodiment, a perspective view of internal and external components of a human ear and a prior art cochlear implant implanted in the human ear.

The components of the human ear 9 that are relevant to the present subject matter and prior art are the pinna 910, the cochlea 920, the auditory nerve 930, the ear canal 940, and the ear drum 950.

The prior art cochlear implant 3 comprises an external microphone 310 configured to receive sound signals, convert the sound signals to electrical sound signals, and transmit electrical energy and data, for example the aforementioned electrical sound signals. The external microphone 310 can be attached to the pinna 910, as shown in FIG. 1. However, it is also possible to attach the external microphone 310 to any item convenient to a user of the prior art cochlear implant 3. The external microphone 310 is electrically connected to an external modulator 320, configured to receive electrical sound signals from the external microphone 310, modulate a carrier signal with the electrical sound signals to produce a modulated electrical carrier signal, and transmit the modulated electrical carrier signal. A common carrier signal that is used in prior art cochlear implants 3 is a radio frequency signal, known as RF signal. The external modulator 320 is electrically connected to an external transmitting antenna 330. The external transmitting antenna 330 is configured to receive the modulated electrical carrier signal from the external modulator 320, convert the modulated electrical carrier signal to a modulated wireless carrier signal, and wirelessly transmit electrical energy and data, for example the aforementioned modulated wireless carrier signal. A common wireless carrier signal that is used in prior art cochlear implants is an electromagnetic RF signal. The external transmitting antenna 330 normally has a coil-like shape. All, the external microphone 310, the external modulator 320, and the external transmitting antenna 330 are external components of the prior art cochlear implant 3. In other words, the external microphone 310, the external modulator 320, and the external transmitting antenna 330 are attached to the skin of the user. However, alternatively, the external transmitting antenna 330 can still be attached to the skin, while the external microphone 310, and alternatively the external modulator 320, can be attached to a clothing of the user. Additional components can be connected to the external components of the prior art cochlear implant 3, in order to facilitate their function. These components include electronics, for example digital signal processor (DSP) chips the selectively filter the sound signals received by the external microphone 310 to prioritize audible speech; and a battery.

The prior art cochlear implant 3 further comprises implanted components, that is components that are implanted under a skin, or in the internal parts of the ear 9, of the user. Thus, the prior art cochlear implant 3 further comprises an internal receiving antenna 340 configured to receive electrical energy and data, for example the aforementioned modulated wireless carrier signal from the external transmitting antenna 330, convert the modulated wireless carrier signal to a modulated electrical carrier signal and transmit electrical energy and data, for example the aforementioned modulated electrical carrier signal. The internal receiving antenna 340 can also have a coil-like structure, and it is implanted under the skin, normally under just above the pinna 910, on the mastoid bone. The prior art cochlear implant 3 further comprises an external magnet 350 placed adjacent to the external transmitting antenna 330 and an internal magnet 360 placed adjacent to the internal receiving antenna 340. The purpose of the external magnet 350 and the internal magnet 360 is to facilitate placement of the external transmitting antenna 330 on the skin in vicinity of the internal receiving antenna 340 that is implanted under the skin, on the mastoid bone. The internal receiving antenna 340 is electrically connected to an internal processor 370, configured to receive the modulated electrical carrier signal from the internal receiving antenna 340, demodulate the modulated electrical carrier signal to produce electrical sound signals, and transmit the electrical sound signals to an electrode array 380. According to one embodiment, the internal processor 370 is in a form of a chip, for example an ASIC chip. Thus, the internal processor 370 is further configured to perform additional tasks relating to controlling the function of the prior art cochlear implant 3, and ensuring proper function of the prior art cochlear implant 3. Some exemplary functions of the internal processor 370 include error check of decoded electrical sound signals to ensure proper decoding, controlling the timing and direction of transmission of the decoded electrical sound signals, and the like. Another implanted component of the prior art cochlear implant 3 is an electrode array 380 that is implanted in the cochlea 920 of the ear 9. The internal processor 370 is electrically connected to the electrode array 380. The electrode array 380 is configured to receive electrical sound signals from the internal processor 370, and stimulate with these electrical sound signals the auditory nerve 930, that is adjacent to the cochlea 920. Then, the auditory nerve 930 transmits the signals that it receives from the electrode array 380 to the brain, and the brain translates these signals to a sense of sound and speech.

One drawback of the prior art cochlear implant 3 is that it includes external parts, as detailed above. There are users that fill annoyed from carrying such external components, whether on their ear's pinna 910, or on a clothing, and on the skin in the vicinity of the pinna 910. Other users can prefer hiding their hearing impairment, and therefore even prefer not to use the prior art cochlear implant 3, and leave their hearing impairment without treatment.

SUMMARY

According to one aspect of the present subject matter, there is provided A hidden cochlear implant system for an ear, comprising:
   a canal unit; and
   an implanted unit,
   wherein the canal unit comprising:
   at least one canal microphone configured to receive sound signals, convert the sound signals to electrical sound signals, and transmit the electrical sound signals;
   a canal modulator configured to receive electrical sound signals, produce a modulated electrical carrier signal, and transmit data in a form of the modulated electrical carrier signal; a canal transmitting antenna configured to transmit electrical energy to the implanted unit; and
   a canal electrical power source,
   wherein the at least one canal microphone is electrically connected to the canal modulator, the canal modulator is electrically connected to the canal transmitting antenna, and the canal electrical power source is electrically connected to any component of the canal unit that requires supply of electrical power,
   and wherein the implanted unit comprising:
   a cochlear receiving antenna configured to be implanted in a middle ear in a vicinity of the ear drum, aside a cochlea, and receive the electrical energy transmitted by the canal transmitting antenna;
   a processor configured to receive data and transmit electrical signals; and
   an electrode array configured to be implanted in the cochlea,
   wherein the cochlear receiving antenna is electrically connected to the processor, and the processor is electrically connected to the electrode array.

According to another preferred embodiment, the processor is configured to be implanted under a skin on a mastoid bone.

According to another preferred embodiment, the cochlear receiving antenna has a coil-like structure, and is configured to receive the electrical energy electromagnetically and wherein the canal transmitting antenna has a coil-like structure, and is configured to transmit the electrical energy electromagnetically.

According to another preferred embodiment, the canal unit is configured to wirelessly transmit the electrical energy and the data, separately, and wherein the implanted unit is configured to receive the electrical energy and data and transmit the data to an auditory nerve through electrode array According to another preferred embodiment, the implanted unit further comprising an additional internal receiving antenna, electrically connected to the processor, wherein the internal receiving antenna is configured to be implanted under a skin on a mastoid bone, and to receive electrical energy and data from an external transmitting antenna.

According to another preferred embodiment, the processor is configured to be implanted aside the cochlea.

According to another preferred embodiment, the canal transmitting antenna is of a type of an optical transmitter, and the cochlear receiving antenna is of a type of optical receiver, wherein the optical transmitter is transferring light energy through the eardrum to the optical receiver located in the middle ear and the optical receiver converts light energy into electrical energy and wherein the electrical energy and data are optically transmitted between the canal transmitting antenna and the cochlear receiving antenna.

According to another preferred embodiment, the canal unit further comprising a canal processor, wherein the at least one canal microphone is electrically connected to the canal processor, and the canal processor is electrically connected to the canal modulator, and wherein the canal processor is configured to receive electrical sound signals from the at least one canal microphone, process the electrical sound signals to produce processed electrical sound signals, and transmit the processed electrical sound signals to the canal modulator.

According to another preferred embodiment, the canal electrical power source is rechargeable.

According to another preferred embodiment, the canal unit is configured to adapt its shape and size to the shape and size of an auditory canal of the ear.

According to another preferred embodiment, the canal unit further comprising at least one grasping element configured to facilitate grasping of the canal unit.

According to another preferred embodiment, the hidden cochlear implant is configured to determine a distance between the canal transmitting antenna and the cochlear receiving antenna, and wherein the distance between the canal transmitting antenna and the cochlear receiving antenna is calculated according to a difference between the level of energy that is transmitted from the canal transmitting antenna and the level of energy received by the cochlear receiving antenna.

According to another preferred embodiment, the hidden cochlear implant system is further comprising an adjusting mechanism configured to change the distance between the canal transmitting antenna and the cochlear receiving antenna.

According to another preferred embodiment, the electrode array is a vibrating electrode array configured to stimulate an auditory nerve of the ear by vibrations.

According to another preferred embodiment, the canal unit further comprising a ventilation channel allowing air to flow into the ear canal.

In accordance to another aspect of the present subject matter, a hidden cochlear implant system for an ear is provided that comprises:
   an external unit;
   a canal unit; and
   an implanted unit,
   wherein the external unit comprises:
   at least one microphone;
   a modulator;
   an electrical power source;
   and wherein the at least one microphone is electrically connected to the modulator, the modulator is electrically connected to the transmitting antenna, and the electrical power source is electrically connected to any component that requires supply of electrical power; and wherein the canal unit comprises:
   a transmitting antenna;
   and wherein the implanted unit comprises:

a cochlear receiving antenna configured to be implanted in a middle ear in a vicinity of a ear drum, aside a cochlea, and receive the electrical energy transmitted by the transmitting antenna;

a processor configured to receive data and transmit electrical signals;

an electrode array configured to be implanted in the cochlea, and wherein the cochlear receiving antenna is electrically connected to the processor, and the processor is electrically connected to the electrode array.

According to another preferred embodiment, the hidden cochlear implant system further comprises an internal receiving antenna, electrically connected to the processor, wherein the internal receiving antenna is configured to be implanted under a skin on a mastoid bone, and to receive electrical energy and data from an external transmitting antenna.

According to another preferred embodiment, the at least one microphone or the modulator or the electrical power source reside within the canal unit.

According to another preferred embodiment, the hidden cochlear implant system further comprises a conduit configured to facilitate implantation of at least one component of the implanted unit wherein the conduit comprises:

an elongated hollow element comprising a lumen; and a pushing element configured to be inserted into the lumen of the elongated hollow element and push at least one component of the implanted unit placed in the lumen.

According to another aspect of the present subject matter, an implanted unit of a hidden cochlear implant system for an ear is provided that comprises:

a cochlear receiving antenna configured to be implanted in a middle ear in a vicinity of the ear drum, aside a cochlea, and receive the electrical energy transmitted by the canal transmitting antenna;

a processor configured to receive data and transmit electrical signals;

an electrode array configured to be implanted in the cochlea; and an additional internal receiving antenna, electrically connected to the processor, wherein the internal receiving antenna is configured to be implanted under a skin on a mastoid bone, and to receive electrical energy and data from an external transmitting antenna wherein the cochlear receiving antenna is electrically connected to the processor, and the processor is electrically connected to the electrode array.

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings:

FIG. 17 schematically illustrates, according to an exemplary embodiment of the present subject matter, a side view of an internal receiving antenna adaptor electrically connected to a cochlear receiving antenna.

FIGS. 18-20 schematically illustrate exemplary embodiments, in accordance with the present subject matter, of a storing member.

DESCRIPTION OF THE PREFERRED EMBODIMENTS

Figure 1:
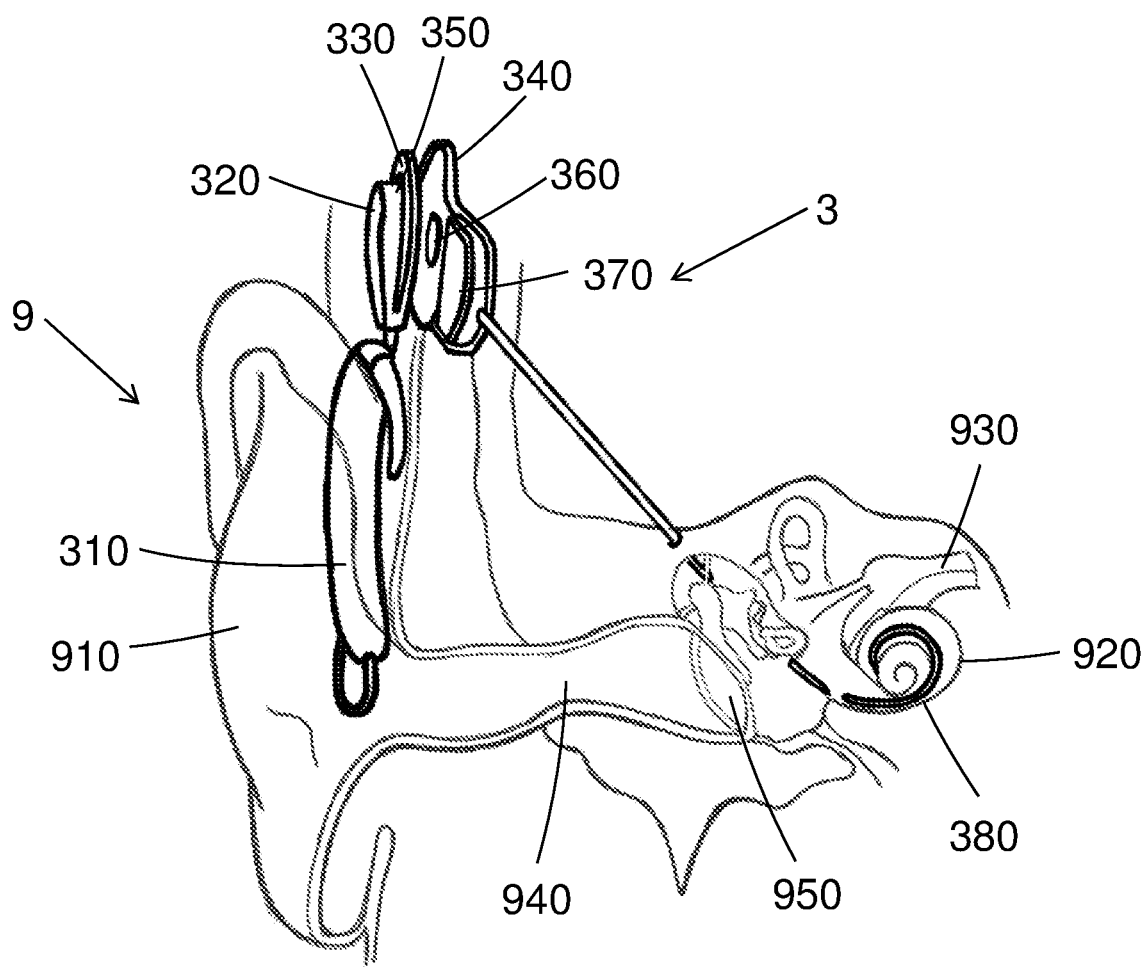
FIG. 1 schematically illustrates, according to an exemplary embodiment, a perspective view of internal and external components of a human ear and a prior art cochlear implant implanted in the human ear.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

Referring now to FIG. 1 schematically illustrating, according to an exemplary embodiment, a perspective view of internal and external components of a human ear and a prior art cochlear implant implanted in the human ear. The present subject matter provides a cochlear implant that does not comprise external components attached to external parts of a user, for example, the user's pinna 910, a clothing of the user, and on the skin of the user in the vicinity of the pinna 910.

The present subject matter further provides, according to some embodiments, a cochlear implant that does not comprise components that are implanted under the skin, for example in the vicinity of the pinna 910, and from the area of the pinna 910 towards the cochlea 920.

The present subject matter provides in addition a cochlear implant that can still be used by users that already have implanted parts of a prior art cochlear implant 3, for example, users that have an internal receiving antenna 340, an internal processor 370, and an electrode array 380, implanted under the skin in the area of the pinna 910, on the mastoid bone, in the cochlea 920, and in-between.

In order to distinguish between the cochlear implant of the present subject matter and the prior art cochlear implant 3, the cochlear implant of the present subject matter is designated hereinafter "hidden cochlear implant system".

According to one embodiment of the present subject matter, components of the hidden cochlear implant system 1 are made of at least one biocompatible material. According to another embodiment, at least components or parts of the hidden cochlear implant system 1 that are exposed to a biological tissue, for example a biological tissue of an ear, are biocompatible. The importance of these embodiments is that since components of the hidden cochlear implant system 1 are configured to be implanted in internal parts of the ear 9, like the cochlea 920, or inserted into the ear canal 940, at least the components or parts of the hidden cochlear implant system 1 that are exposed to a biological tissue have to be made of at least one biocompatible material in order to avoid rejection response to the hidden cochlear implant system 1, inflammation, and the like. Some exemplary biocompatible material of which components or parts of the hidden cochlear implant system 1 can be made, include, but not limited to, biocompatible metals such as stainless steel, cobalt alloys, titanium alloys, and the like; biocompatible ceramics such as aluminum oxide, zirconia, calcium phosphates, and the like; biocompatible polymers such as silicones, poly ethylene, poly vinyl chloride, polyurethanes, polylactides and the like; and biocompatible natural polymers such as collagen, gelatin, elastin, silk, polysaccharides, and the like. It should be noted that this list of biocompatible materials of which components or parts of the hidden cochlear implant system 1 can be made should not be considered a limiting the scope of the present subject matter, but rather to serve only as an exemplary list of biocompatible materials.

Figure 14:
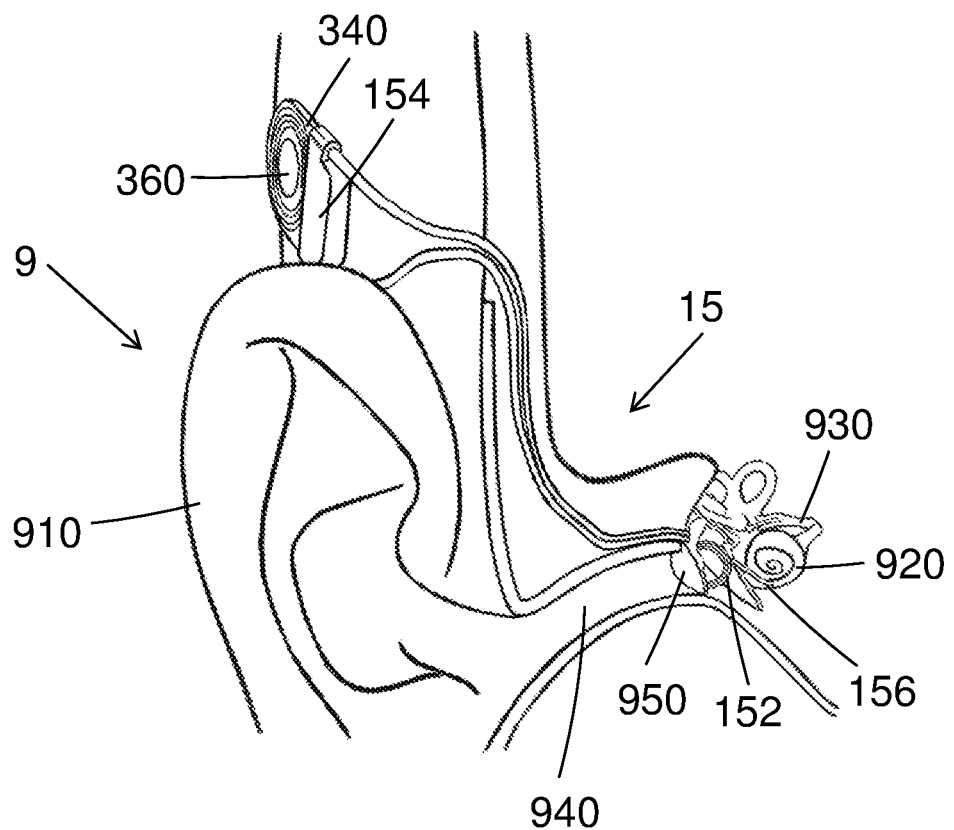
FIG. 14 schematically illustrates, according to an exemplary embodiment of the present subject matter, a perspective view of internal components of a human ear and another embodiment of an implanted unit that is implanted partially in the vicinity of the cochlea, and partially implanted under the skin, in the vicinity of the pinna, on the mastoid bone.
Figure 15:
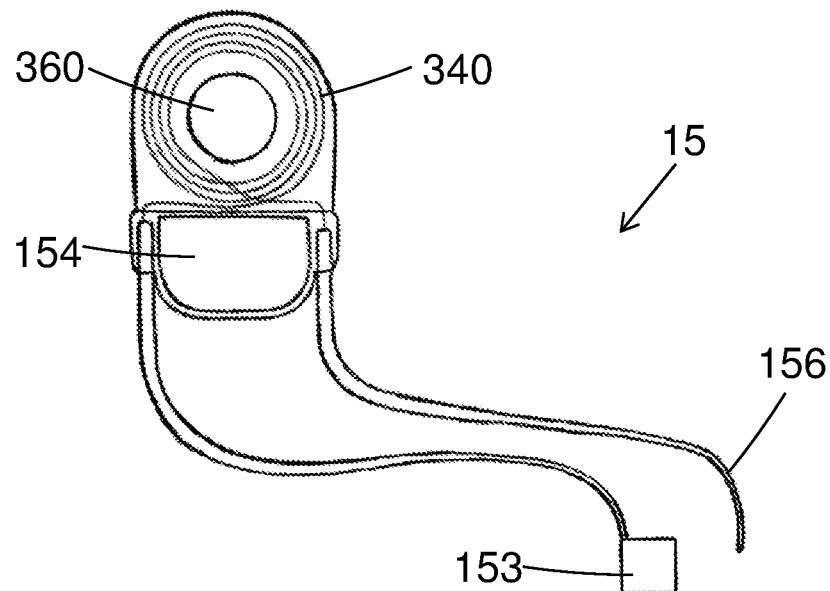
FIG. 15 schematically illustrates, according to an exemplary embodiment of the present subject matter, a perspective see-through view of a side view of an implanted unit of a hidden cochlear implant system, further comprising a cochlear optical receiver instead of the cochlear receiving antenna.
Figure 16:
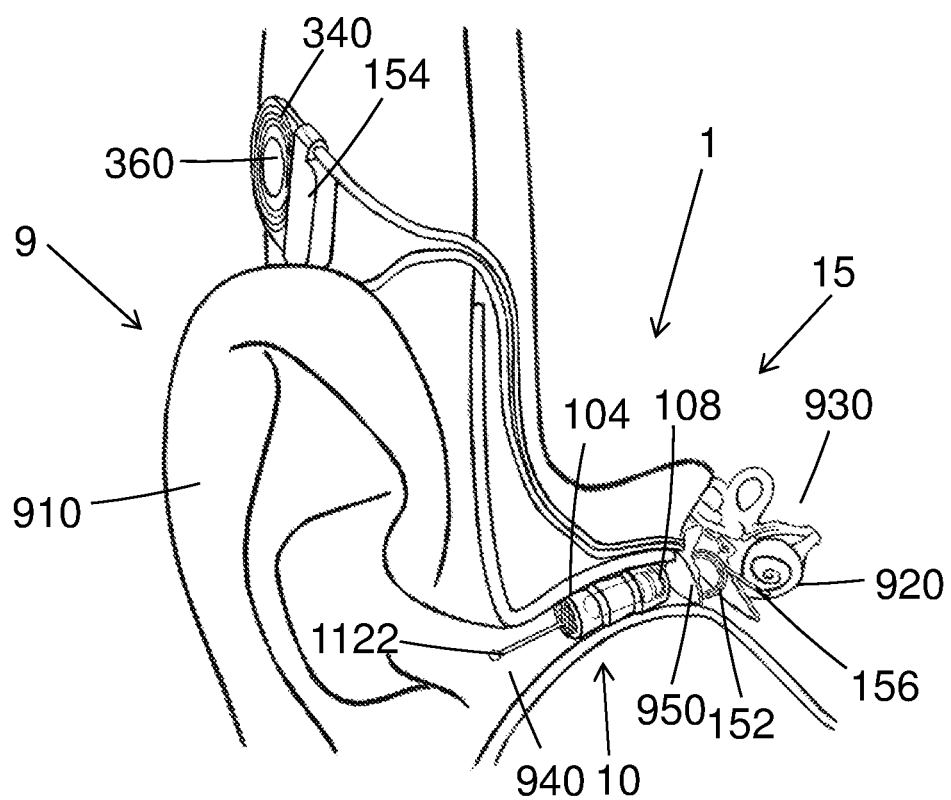
FIG. 16 schematically illustrates, according to an exemplary embodiment of the present subject matter, a perspective view of internal components of a human ear and an implanted unit implanted partially in the vicinity of the cochlea, and partially implanted under the skin, in the vicinity of the pinna, on the mastoid bone, as well as a canal unit inserted in the ear canal.

According to one embodiment, the hidden cochlear implant system 1, shown as a whole in FIG. 16, comprises a canal unit 10, shown in FIGS. 2-8, and an implanted unit 15, shown in FIGS. 9-15.

Figure 2:
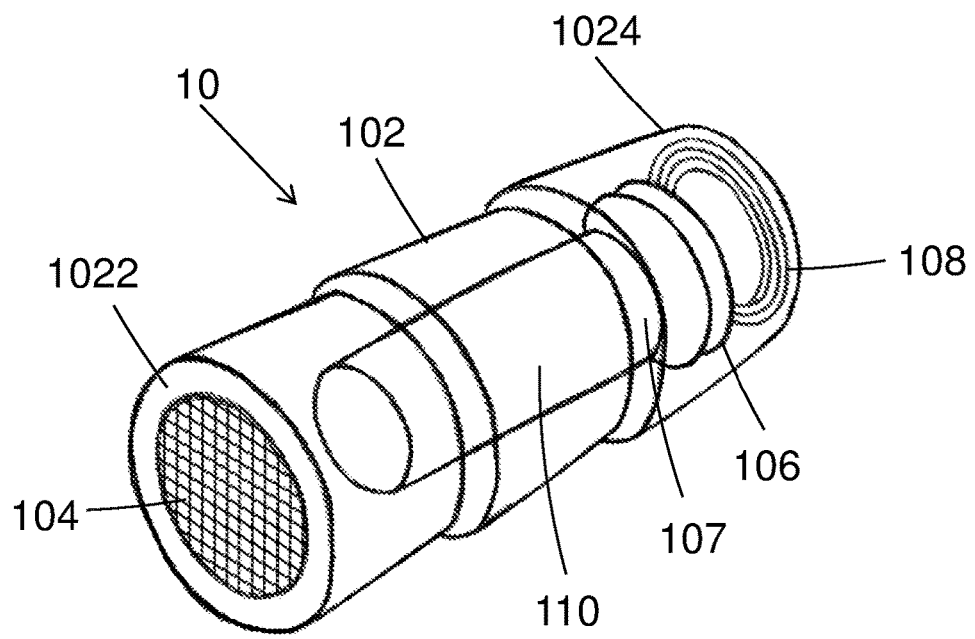
FIG. 2 schematically illustrates, according to an exemplary embodiment of the present subject matter, a perspective see-through view of a canal unit of a hidden cochlear implant system.

Referring now to FIG. 2 schematically illustrating, according to an exemplary embodiment of the present subject matter, a perspective see-through view of a canal unit of a hidden cochlear implant system.

Figure 8:
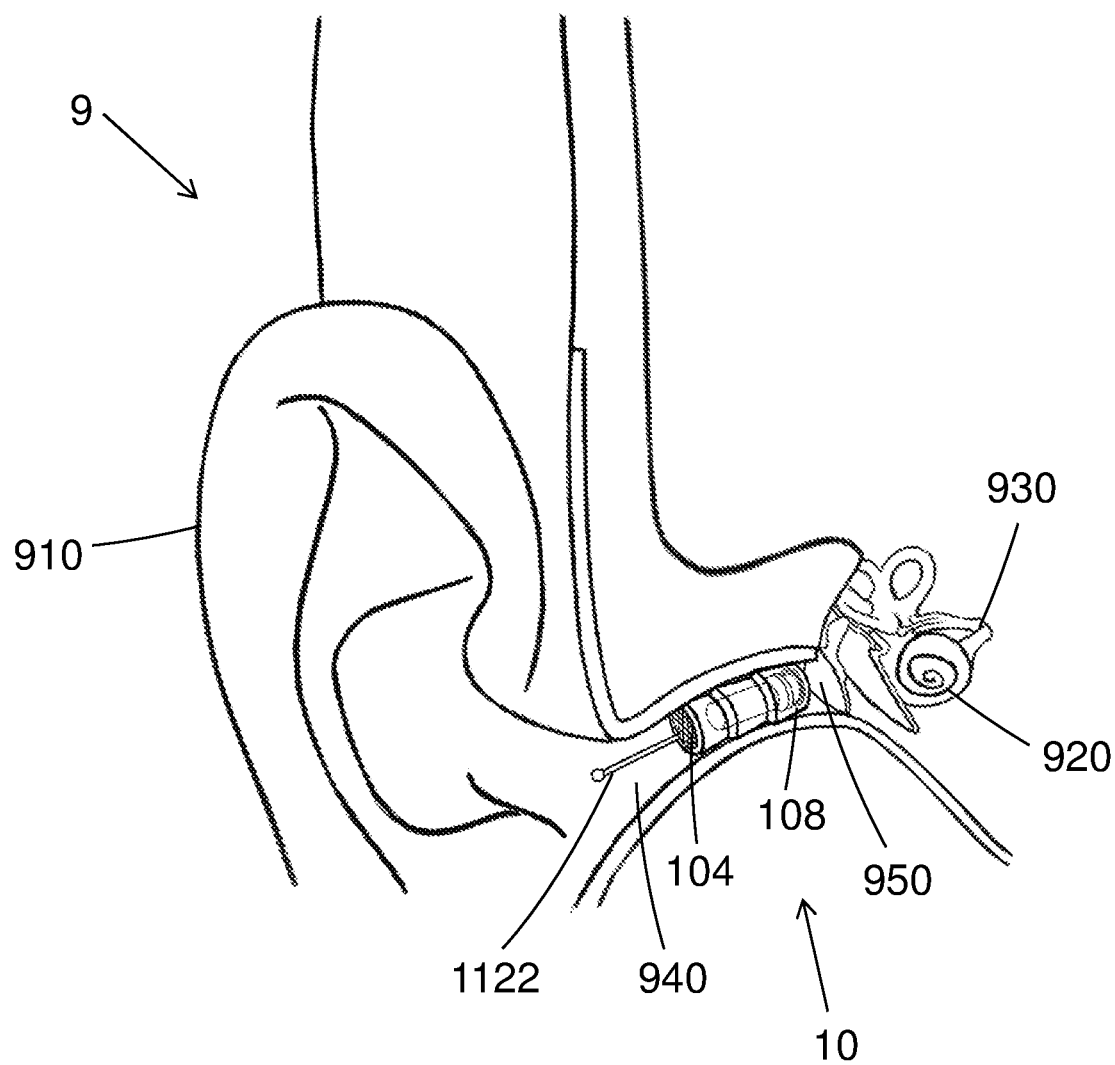
FIG. 8 schematically illustrates, according to an exemplary embodiment of the present subject matter, a perspective view of internal and external components of a human ear and a canal unit inserted in the ear canal.

According to one embodiment, the canal unit 10 is configured to be inserted into an ear canal 940 of an ear 9 (as shown in FIG. 8), wherein the canal unit 10 is further configured to receive sound signals that enter into the ear canal 940, convert the sound signals to electrical sound signals, modulate a carrier wave with the electrical sound signals to obtain a modulated carrier wave, and wirelessly transmit electrical energy and data, for example the aforementioned modulated carrier wave. The canal unit 10 is inserted into an ear canal 940 during a surgical procedure.

According to one embodiment, at least part of the implanted unit 15 is configured to be implanted in a vicinity to a cochlear 920 of an ear 9. During such surgical procedure, in order to allow a large space for the implanted unit 15 in the middle ear, the tiny bones called the Malleus, Incus and Stapes can be removed. According to another embodiment, the implanted unit 15 is configured to receive electrical energy and data, for example the aforementioned modulated carrier wave that is transmitted by the canal unit 10, demodulate the modulated carrier wave to obtain electrical sound signals, and stimulate an auditory nerve 930 with the electrical sound signals.

According to one embodiment, the canal unit 10 replaces the external components of the prior art cochlear implant 3 of FIG. 1, which were described above. In other words, usage of the canal unit 10 can negate usage of the external components of the prior art cochlear implant 3. For example, the canal unit 10 replaces the prior art external microphone 310, the prior art external modulator 320, the prior art external transmitting antenna 330, the prior art external magnet 350, the prior art electronics, such as the prior art digital signal processor (DSP) chips, and any other external component that can be part of the prior art cochlear implant 3. A person skilled in the art would appreciate the benefits and advantages of the hidden cochlear implant system 1 of the present subject matter over the prior art cochlear implant 3. Firstly, the hidden cochlear implant system 1 does not comprise external components that are easily visible. Thus, a user can use the hidden cochlear implant system 1 without any one to notice that. This is extremely beneficial and advantageous, especially for people that would not use a prior art cochlear implant 3 because of the annoyance related to carrying external components.

According to one embodiment, the shape and size of the canal unit 10 is configured to adapt to a shape and size of an ear canal 940 of a user. According to another embodiment, the canal unit 10 is elastic so it could adapt its shape and size to the shape and size of the ear canal 940 of the user.

According to one embodiment, the canal unit 10 has a hollow cylindrical shape comprising an outward side 1022 and an inward side 1024. The outward side 1022 of the canal unit 10 is configured to point towards the pinna 910 of the ear 9, namely in an outward direction relative to the ear canal 940, when the canal unit 10 resides in the ear canal 940. The inward side 1024 of the canal unit 10 is configured to point toward an inner part of the ear, more particularly, toward the ear drum 950 and the cochlea 920, when the canal unit 10 resides in the ear canal 940. According to another embodiment, components of the canal unit 10, detailed hereinafter, are configured to be accommodated in an inner space formed by the hollow cylindrical shape of the canal unit 10.

According to one embodiment, the canal unit 10 comprises at least one canal microphone 104, a canal modulator 106, a canal transmitting antenna 108, and a canal electrical power source 110, wherein the at least one canal microphone 104 is electrically connected to the canal modulator 106, the canal modulator 106 is electrically connected to the canal transmitting antenna 108, and the canal electrical power source 110 is electrically connected to any component of the canal unit 10 that requires supply of electrical power, for example the at least one canal microphone 104, the canal modulator 106, and the like.

According to one embodiment, the at least one canal microphone 104 is configured to receive sound signals, convert the sound signals to electrical sound signals, and transmit the electrical sound signals to the canal modulator 106. According to another embodiment, the at least one canal microphone 104 is configured to be placed at the outward side 1022 of the canal unit 10, so the at least one canal microphone 104 would be able to receive sound signals that enter into the ear canal 940.

According to one embodiment, the canal modulator 106 is configured to receive electrical sound signals from the at least one canal microphone 104, modulate an electrical carrier signal with the electrical sound signals to produce a modulated electrical carrier signal, and transmit the modulated electrical carrier signal to the canal transmitting antenna 108.

According to one embodiment, the canal transmitting antenna 108 is configured to receive the modulated electrical carrier signal from the canal modulator 106, convert the modulated electrical carrier signal to a modulated wireless carrier signal, and wirelessly transmit electrical energy and data, for example the aforementioned modulated wireless carrier signal. According to another embodiment, the canal transmitting antenna 108 is configured to wirelessly transmit any type of a wireless carrier signal known in the art, for example an electromagnetic RF signal, short-wavelength ultra-high frequency (UHF) radio waves—a technology known as "Bluetooth", an optical carrier signal, and the like. According to one embodiment, mentioned above, the canal transmitting antenna 108 is configured to transmit electrical energy and data, for example a modulated wireless carrier signal. According to another embodiment, the canal transmitting antenna 108 is configured to transmit electrical energy, for example in a form of a non-modulated wireless carrier signal, namely a carrier signal only. According to one embodiment, the canal transmitting antenna 108 can have any shape known in the art. According to a preferred embodiment, the canal transmitting antenna 108 has a coil-like shape. According to another preferred embodiment, the canal transmitting antenna 108 is configured to be placed at the inward side 1024 of the canal unit 10, so the canal transmitting antenna 108 would be able to transmit electrical energy, for example in a form of a wireless carrier signal, and data, for example a modulated wireless carrier signal, toward the ear drum 950 and the cochlea 920 as will be described hereinafter.

According to one embodiment, the canal transmitting antenna 108 can further comprise a ferromagnetic ferrite in order to improve the efficiency of transmission of the canal transmitting antenna 108.

According to one embodiment, the canal unit 10 can further comprise a canal processor 107, wherein the at least one canal microphone 104 is electrically connected to the canal processor 107, and the canal processor 107 is electrically connected to the canal modulator 106.

According to another embodiment, the canal processor 107 is configured to receive electrical sound signals from the at least one canal microphone 104, process the electrical sound signals to produce processed electrical sound signals, and transmit the processed electrical sound signals to the canal modulator 106. An exemplary process of the electrical sound signals that can be performed by the canal processor 107 is selective filtering of electrical sound signals to prioritize electrical sound signals originating from audible speech. Any type of processor that can perform the required processing of electrical sound signals can serve as a canal processor 107. According to a preferred embodiment, the canal processor 107 comprises DSP chips. Another exemplary canal processor 107 is a completely in canal (CIC).

As mentioned above, the canal unit 10 comprises a canal electrical power source 110. Any type of electrical power source known in the art can serve as a canal electrical power source 110. For example, the canal electrical power source 110 can be a battery, a rechargeable battery, and the like. According to a preferred embodiment, the canal electrical power source 110 is a rechargeable battery.

According to one embodiment, the canal unit 10 further comprises a casing 102 configured to accommodate components of the canal unit 10, for example the at least one canal microphone 104, the canal modulator 106, the canal transmitting antenna 108, the canal electrical power source 110, the canal processor 107, and the like. According to another embodiment, the casing 102 is configured to determine the cylindrical shape of the canal unit 10. According to yet another embodiment, the casing 102 is configured to protect the components that are accommodated in the casing 102.

According to one embodiment, the casing 102 has a hollow elongated shape defining a space. According to another embodiment, components of the canal unit 10 are configured to be accommodated in the space of the casing 102. According to yet another embodiment, the case 102 further comprises an outward side 1022 and an inward side 1024. The outward side 1022 of the casing is configured to point towards the pinna 910 of the ear 9, namely in an outward direction relative to the ear canal 940, when the canal unit 10 resides in the ear canal 940. The inward side 1024 of the casing 102 is configured to point toward an inner part of the ear, more particularly, toward the ear drum 950 and the cochlea 920. According to some embodiments, the canal unit 10 is configured to be inserted into the ear canal 940 until the inward side 1024 of the casing 102 is in close vicinity to the ear drum 950, as can be seen for example in FIG. 8 hereinafter.

According to one embodiment, the casing 102, accommodating components of the canal unit 10, is configured to be inserted into the ear canal 940 of a human ear 9. According to yet another embodiment, the shape and size of the casing 102 is configured to adapt to a shape and size of an ear canal 940 of a user. According to still another embodiment, the casing 102 is elastic so it could adapt its shape and size to the shape and size of the ear canal 940 of the user. Thus, the casing 102 is made of any material known in the art that is elastic, for example soft plastic, fabric, silicon and the like, in addition to being made of at least one compatible material, according to some embodiments, as described above. According to a preferred embodiment, the casing 102 is made of silicon. According to a further embodiment, the casing 102 is substantially cylindrical similarly to the substantial cylindrical shape of the ear canal 940.

According to one embodiment, the canal unit 10 can further comprise at least one grasping element 112 configured to facilitate grasping of the canal unit 10, for example during handling of the canal unit 10, insertion of the canal unit 10 into the ear canal 940, or removal of the canal unit 10 from the ear canal 940. Any type of component that is configured to facilitate grasping of the canal unit 10 is under the scope of the present subject matter. Here is a description of some exemplary components that are configured to facilitate grasping of the canal unit 10.

Figure 3:
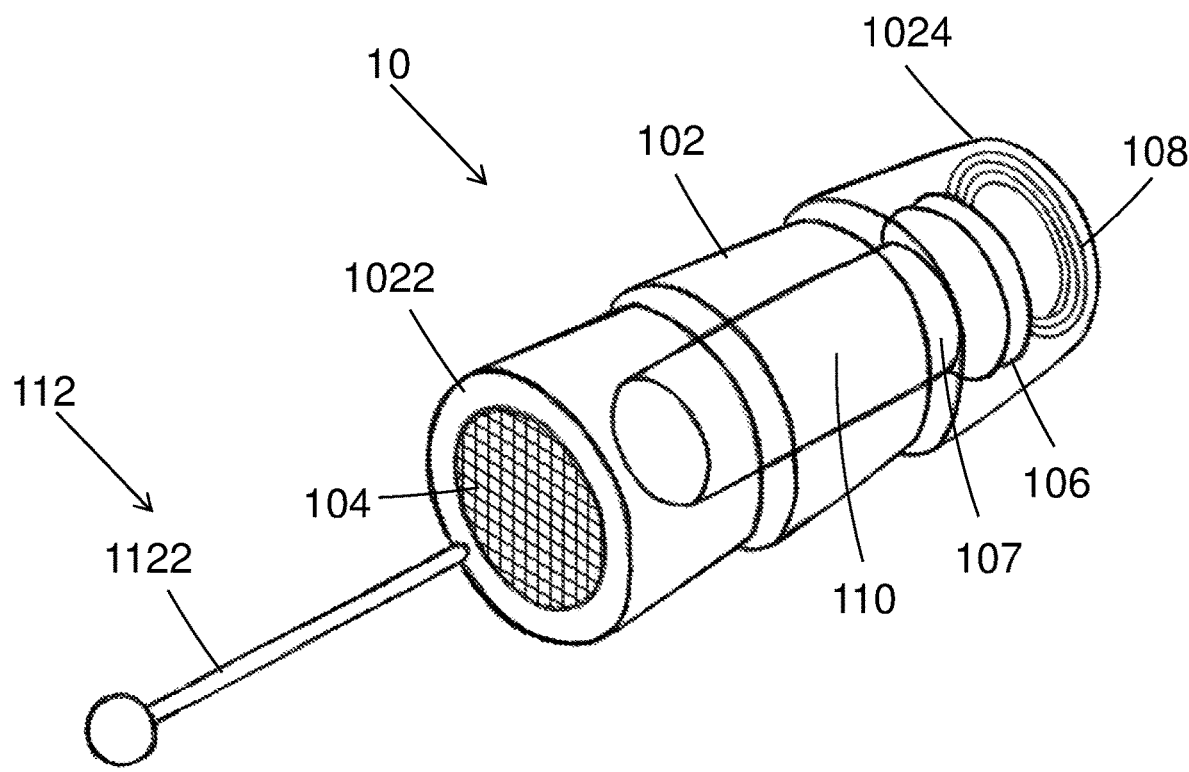
FIG. 3 schematically illustrates, according to an exemplary embodiment of the present subject matter, a perspective see-through view of a canal unit of a hidden cochlear implant system, further comprising a handle.

Referring now to FIG. 3 schematically illustrating, according to an exemplary embodiment of the present subject matter, a perspective see-through view of a canal unit of a hidden cochlear implant system, further comprising a handle.

According to one embodiment, the handle 1122 is configured to be grasped, for example during handling of the canal unit 10, insertion of the canal unit 10 into the ear canal 940, or during removal of the canal unit 10 from the ear canal 940. According to another embodiment, the handle 1122 is configured to be grasped by a tool used for handling the canal unit 10, inserting the canal unit 10 into the ear canal 940, or removing the canal unit 10 from the ear canal 940. For example, the handle 1122 is configured to be grasped by tweezers, forceps, fingers of a user, and the like. According to a further embodiment, the handle 1122 is positioned at any place on the canal unit 10 that is suitable for fulfillment of the purpose of using the handle 1122. According to a preferred embodiment, illustrated for example in FIG. 3, the handle 1122 is attached to the outward side 1022 of the canal unit 10. This position of the handle 1122 is preferable because it allows grasping of the canal unit 10 during insertion of the canal unit 10 into the ear canal 940, or during removal of the canal unit 10 from the ear canal 940.

Figure 4:
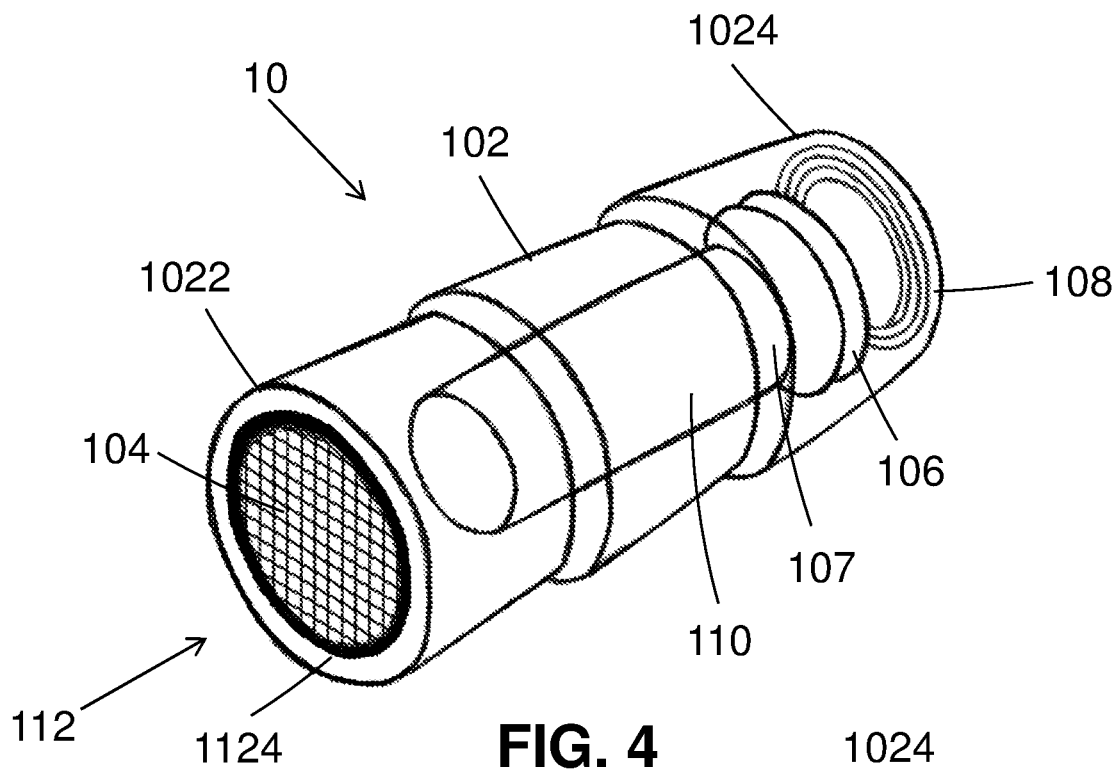
FIG. 4 schematically illustrates, according to an exemplary embodiment of the present subject matter, a perspective see-through view of a canal unit of a hidden cochlear implant system, further comprising an attractable element.

Referring now to FIG. 4 schematically illustrating, according to an exemplary embodiment of the present subject matter, a perspective see-through view of a canal unit of a hidden cochlear implant system, further comprising an attractable element.

According to one embodiment, the attractable element 1124 is configured to be attracted by employing a magnetic force, for example during handling of the canal unit 10, insertion of the canal unit 10 into the ear canal 940, or during removal of the canal unit 10 from the ear canal 940. Thus, according to another embodiment, the attractable element 1124 is made of any material known in the art that is attractable by a magnet, for example iron, nickel, cobalt, gadolinium, dysprosium, and alloys comprising the same. According to yet another embodiment, the attractable element 1124 is magnetic. Thus, the attractable element 1124 is configured to be attracted by any tool known in the art that comprises a magnet, or comprises a material that is attractable by a magnet, and is further suitable for handling the canal unit 10, inserting the canal unit 10 into the ear canal 940, or removing the canal unit 10 from the ear canal 940. According to a further embodiment, the attractable element 1124 can be a piece of a material that is attractable by a magnet, or a magnetic material. According to yet a further embodiment, the attractable element 1124 is positioned at any place on the canal unit 10 that is suitable for fulfillment of the purpose of using the attractable element 1124. According to a preferred embodiment, illustrated for example in FIG. 4, the attractable element 1124 is positioned at the outward side 1022 of the canal unit 10. This position of the attractable element 1124 is preferable because it allows grasping of the canal unit 10 during insertion of the canal unit 10 into the ear canal 940, or during removal of the canal unit 10 from the ear canal 940. According to another preferred embodiment, the attractable element 1124 can have a ring-like shape, as can be seen, for example, in FIG. 4.

Figure 5:
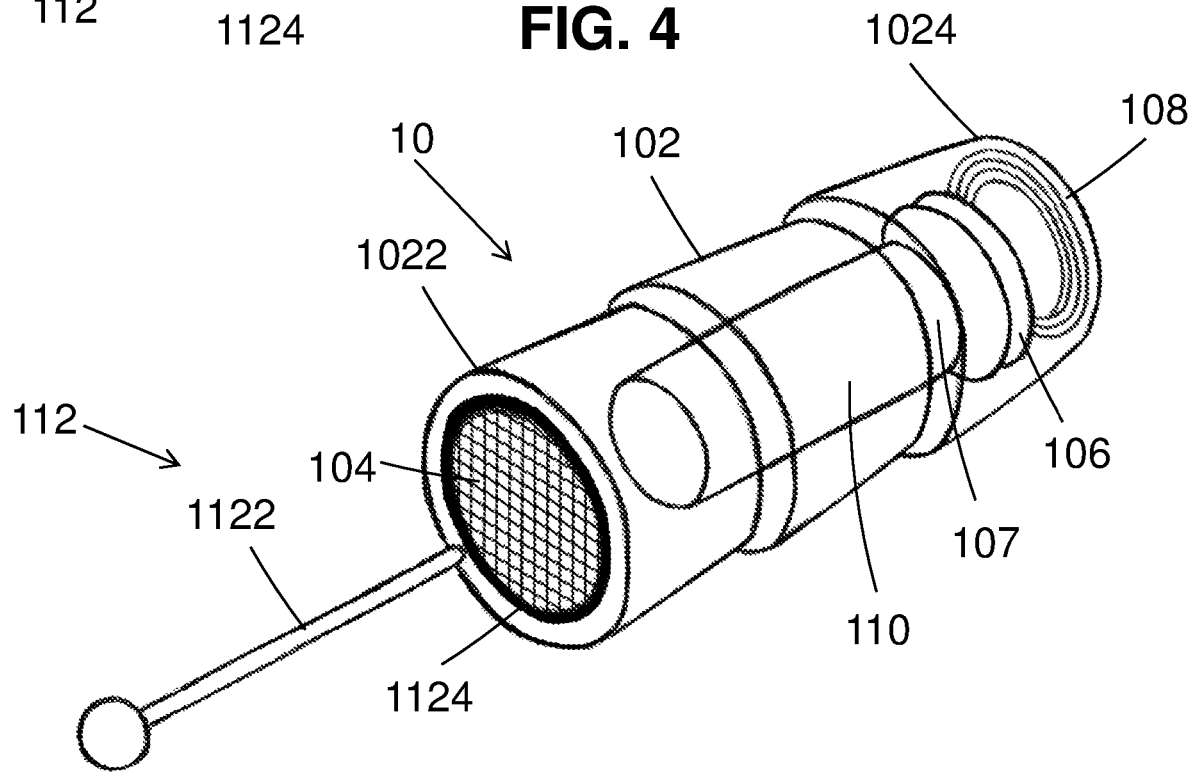
FIG. 5 schematically illustrates, according to an exemplary embodiment of the present subject matter, a perspective see-through view of a canal unit of a hidden cochlear implant system, further comprising a handle and an attractable element.

Referring now to FIG. 5 schematically illustrating, according to an exemplary embodiment of the present subject matter, a perspective see-through view of a canal unit of a hidden cochlear implant system, further comprising a handle and an attractable element.

According to one embodiment, the canal unit 10 comprises multiple components configured to facilitate grasping of the canal unit 10, for example during handling of the canal unit 10, insertion of the canal unit 10 into the ear canal 940, or removal of the canal unit 10 from the ear canal 940. Thus, as can be seen in FIG. 5, the canal unit 10 can further comprise the handle 1122 as described above and shown in FIG. 3, and the attractable element 1124 as described above, and shown in FIG. 4.

Figure 6:
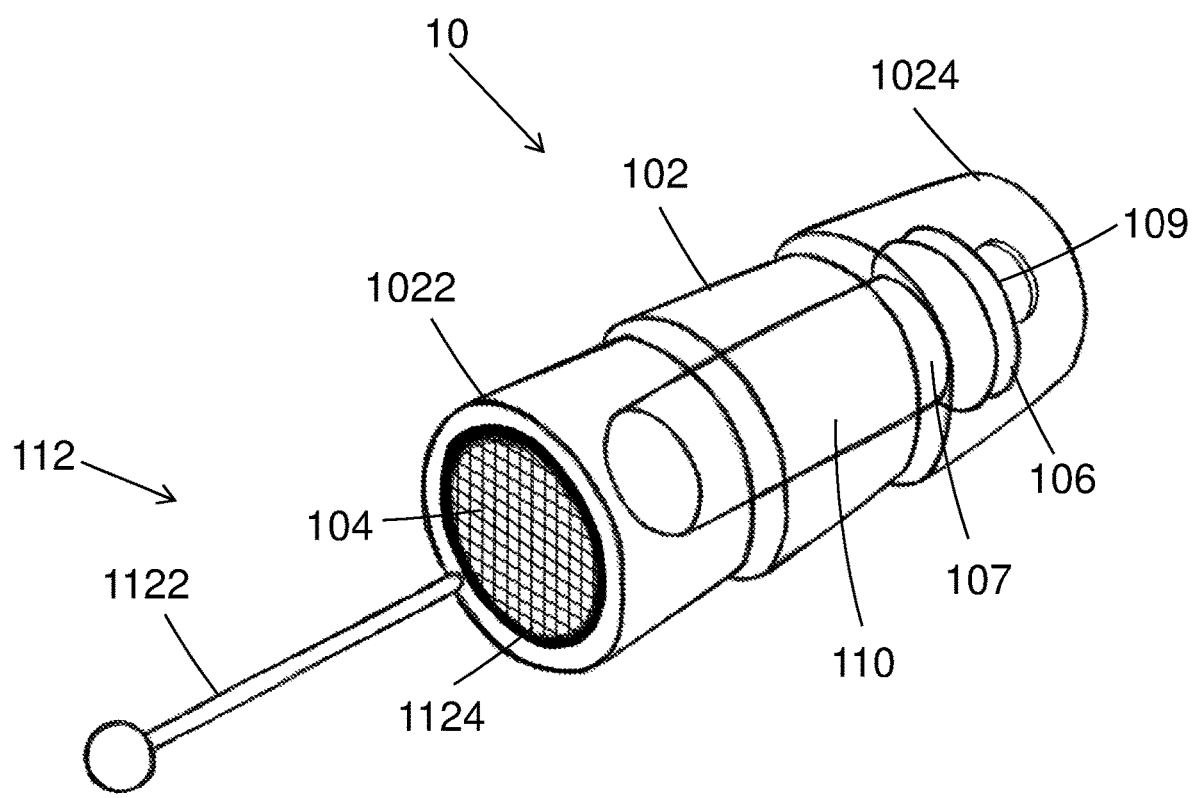
FIG. 6 schematically illustrates, according to an exemplary embodiment of the present subject matter, a perspective see-through view of a canal unit of a hidden cochlear implant system, further comprising a canal optical transmitter instead of the canal transmitting antenna.

Referring now to FIG. 6 schematically illustrating, according to an exemplary embodiment of the present subject matter, a perspective see-through view of a canal unit of a hidden cochlear implant system, further comprising a canal optical transmitter instead of the canal transmitting antenna. It should be noted that the drum 950 is transparent and allows passage of light therethrough.

As described above, the canal transmitting antenna 108 is configured to transmit electrical energy, for example in a form of wireless carrier signal, and data, for example in a form of a modulated wireless carrier signal. Any type of wireless transmission of electrical energy and data from the canal unit 10 is under the scope of the present subject matter, for example transmission of optical energy and the like. FIG. 6 illustrates a canal unit 10 comprising a canal optical transmitter 109 instead of the canal transmitting antenna 108. Any type of optical transmitter is under the scope of the present subject matter, for example light emitting diode (LED) and the like. Accordingly, the receiving antenna 152 functions as an optical receiver that is configured to receive the optical energy and transform the optical energy to electrical energy. Any type of optical receiver is under the scope of the present subject matter, for example a photo-electric cell and the like.

According to one embodiment, the canal unit 10 is configured to be divided to multiple parts, wherein the multiple parts are configured to reassemble to form a complete canal unit 10.

Figure 7A:
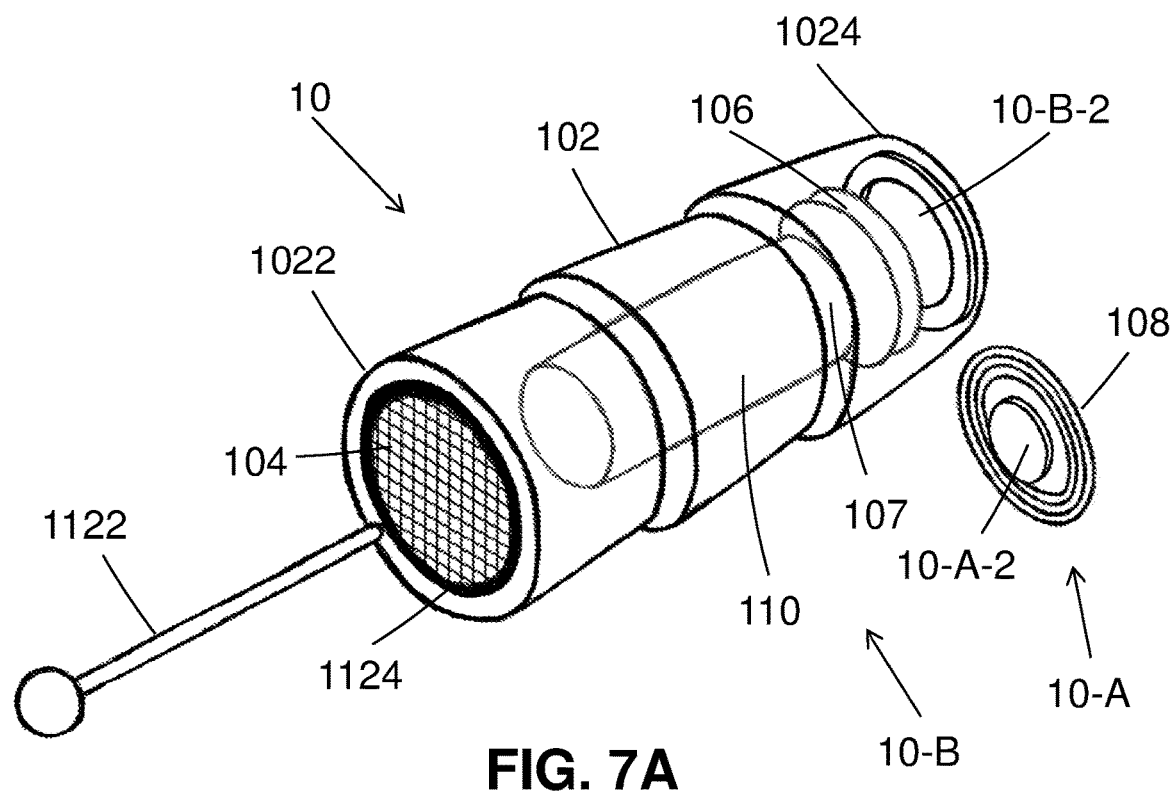
FIG. 7A schematically illustrates, according to an exemplary embodiment of the present subject matter, a perspective see-through view of a canal unit of a hidden cochlear implant system divided to two parts.

Referring now to FIG. 7A schematically illustrating, according to an exemplary embodiment of the present subject matter, a perspective see-through view of a canal unit of a hidden cochlear implant system divided into two parts.

Figure 7B:
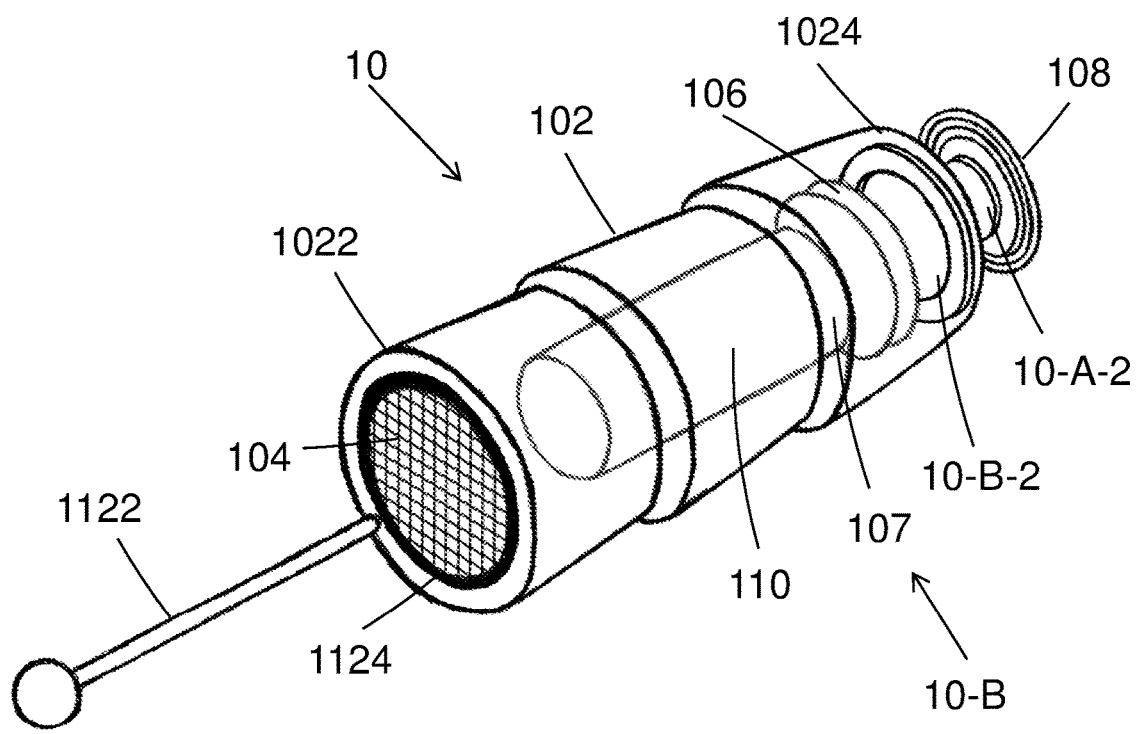
FIG. 7B schematically illustrates, according to an exemplary embodiment of the present subject matter, a perspective see-through view of a canal unit of a hidden cochlear implant system divided to two parts that are partially reassembled.

Referring now to FIG. 7B schematically illustrating, according to an exemplary embodiment of the present subject matter, a perspective see-through view of a canal unit of a hidden cochlear implant system divided into two parts that are partially reassembled.

According to one embodiment, the components of the canal unit 10 can be distributed in any combination between the parts of the canal unit 10, wherein the parts are divided one from the other. The embodiment illustrated in FIGS. 7A-B is exemplary only and should not be considered as limiting the scope of the present subject matter. As can be seen in FIG. 7A, the canal unit 10 is divided into two parts—a first canal unit part 10-A, and a second canal unit part 10-B. According to another embodiment, the first canal unit part 10-A comprises the canal transmitting antenna 108, while the second canal unit part 10-B comprises the other components of the canal unit 10 described above, namely at least the at least one microphone 104, the canal modulator 106, and the canal electrical power source 110. As can be seen in FIGS. 7A-B, the second canal unit part 10-B can further comprise additional components of the canal unit 10. Thus, during insertion of the canal unit 10 into the ear canal 940 of a user, the first canal unit part 10-A can be inserted firstly and positioned in the ear canal 940, adjacent to the ear drum 950. Then, the second canal unit part 10-B can be inserted into the ear canal 940 and reassembled with the first canal unit part 10-A, as shown in FIG. 7B. In order to facilitate the reassembly of the parts of the canal unit 10, the canal unit 10 can further comprise, according to some embodiments, mechanisms for attaching the parts one to the other. For example, as can be seen in FIG. 7A, a mechanism for attaching the parts one to the other can be a male-female mechanism. Thus, the first canal unit part 10-A can comprise a male member 10-A-2, and the second canal unit part 10-B can comprise a female member 10-B-2 that is configured to attach to the male member 10-A-2. Of course, an opposite orientation of the male and female members is also under the scope of the present subject matter.

Referring now to FIG. 8 schematically illustrating, according to an exemplary embodiment of the present subject matter, a perspective view of internal and external components of a human ear and a canal unit inserted in the ear canal.

FIG. 8 illustrating a canal unit 10 inserted in the ear canal 940 of an ear 9 of a user. The canal unit 10 that is illustrated in FIG. 8 comprises inter alia a handle 1122. However, it should be noted that this embodiment of the canal unit 10 inserted in the ear canal 940 is only exemplary, and should not be considered as limiting the scope of the present subject matter. Any embodiment of the canal unit 10, described herein, is similarly configured to be inserted in the ear canal 940.

As can be seen in FIG. 8, the outward side 1022 of the canal unit 10 points toward the pinna 910. As a result, the at least one canal microphone 104 residing at the outward side 1022 of the canal unit 10 can easily receive sound signals that enter into the ear canal 940. In addition, an at least one component configured to facilitate grasping of the canal unit 10, for example a handle 1122, an attractable element 1124, or a combination thereof, that reside at the outward side 1022 of the canal unit 10, can be easily grasped, or attracted by an appropriate tool that is inserted into the ear canal 940 through the pinna 910. As can further be seen in FIG. 8, the inward side 1024 of the canal unit 10 points toward the ear drum 950 and the cochlea 920. As a result, the canal transmitting antenna 108 residing at the inward side 1024 of the canal unit 10 can transmit electrical energy, for example in a form of a wireless carrier signal, and data, for example in a form of a modulated wireless carrier signal, toward the ear drum 950 and the cochlea 920.

Figure 9:
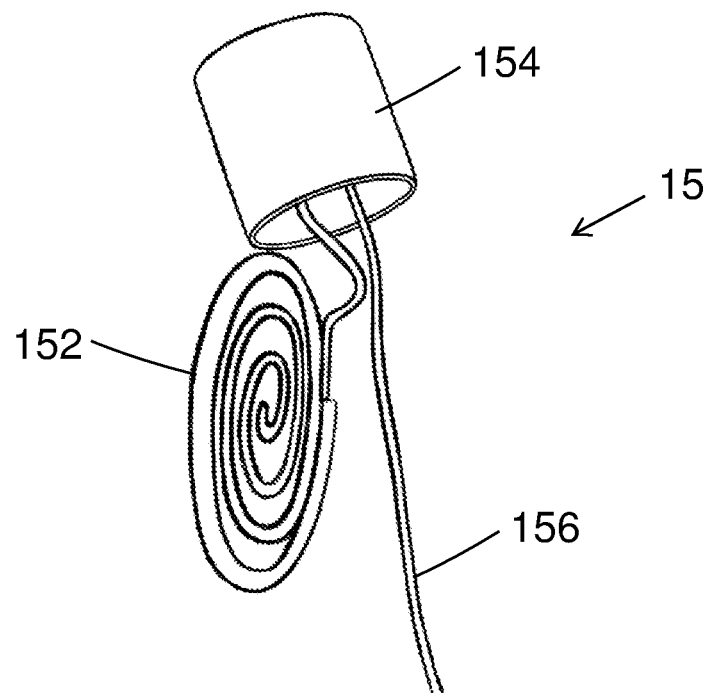
FIG. 9 schematically illustrates, according to an exemplary embodiment of the present subject matter, a side view of an implanted unit of a hidden cochlear implant system, the implanted unit comprising a processor that is configured to be implanted in the vicinity of the cochlea.

Referring now to FIG. 9 schematically illustrating, according to an exemplary embodiment of the present subject matter, a side view of an implanted unit of a hidden cochlear implant system, the implanted unit comprising a processor that is configured to be implanted in the vicinity of the cochlea.

Figure 10:
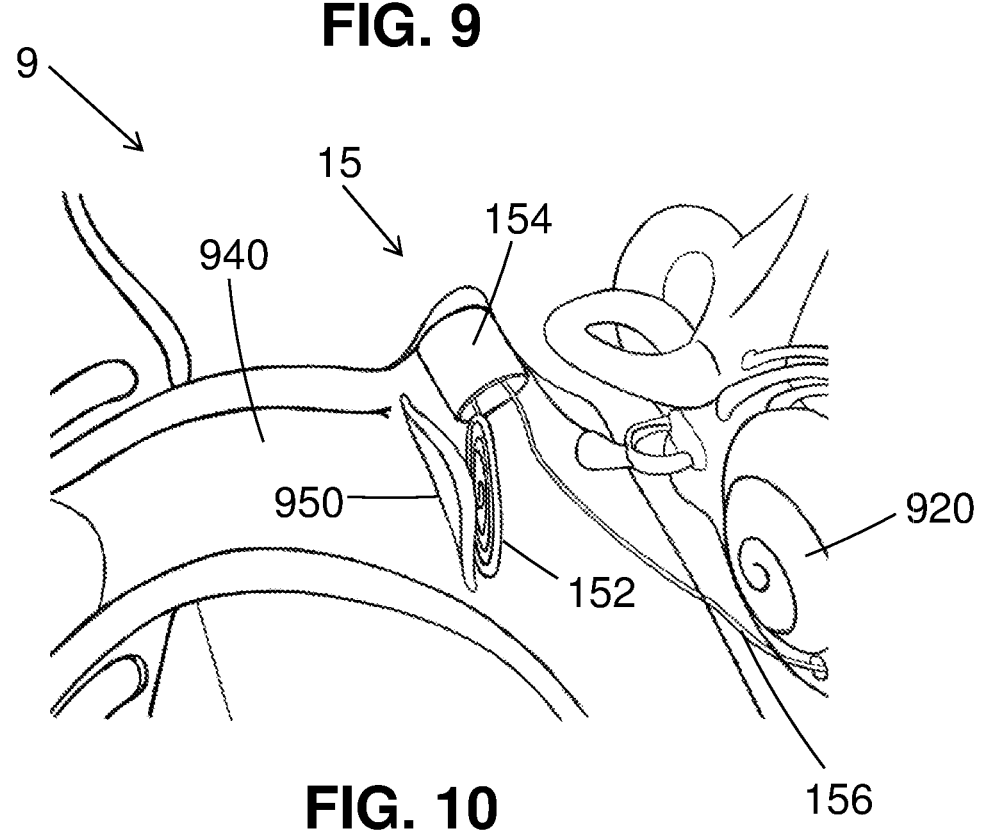
FIG. 10 schematically illustrates, according to an exemplary embodiment of the present subject matter, a perspective view of internal components of a human ear and an implanted unit implanted in the vicinity of the cochlea, the implanted unit comprising a processor that is configured to be implanted in the vicinity of the cochlea.

Referring now to FIG. 10 schematically illustrating, according to an exemplary embodiment of the present subject matter, a perspective view of internal components of a human ear and an implanted unit implanted in the vicinity of the cochlea, the implanted unit comprising a processor that is configured to be implanted in the middle ear in the vicinity of the cochlea.

According to one embodiment, at least part of the implanted unit 15 is configured to be implanted in a cochlea 920 of an ear 9 of a user. According to another embodiment, the implanted unit 15 comprises a cochlear receiving antenna 152, a processor 154 and an electrode array 156, wherein the cochlear receiving antenna 152 is electrically connected to the processor 154, and the processor 154 is electrically connected to the electrode array 156.

According to one embodiment, the cochlear receiving antenna 152 is configured to receive electrical energy, for example in a form a wireless carrier signal, and data, for example in a form of a modulated wireless carrier signal, that is wirelessly transmitted by the canal transmitting antenna 108, convert the wireless carrier signal to an electrical carrier signal, and transmit the electrical carrier signal to the processor 154. The wireless carrier signal can be modulated; or not modulated, namely be only electrical energy, as described above. According to one embodiment, the cochlear receiving antenna 152 can have any shape known in the art. According to a preferred embodiment, the cochlear receiving antenna 152 has a coil-like shape. According to another preferred embodiment, the cochlear receiving antenna 152 is configured to be implanted in the middle ear in the vicinity of the ear drum 950 aside the cochlea 920.

According to one embodiment, the processor 154 is configured to receive a modulated electrical carrier signal from the cochlear receiving antenna 152, demodulate the modulated electrical carrier signal to produce electrical sound signals, and transmit the electrical sound signals to the electrode array 156. According to one embodiment, the processor 154 is in a form of a chip, for example an ASIC chip, as known in the art. Thus, the processor 154 is further configured to perform additional tasks relating to controlling the function of the hidden cochlear implant system 1, and ensuring proper function of the hidden cochlear implant system 1. Some exemplary functions of the processor 154 include error check of decoded electrical sound signals to ensure proper decoding, controlling the timing and direction of transmission of the decoded electrical sound signals, and the like.

According to one embodiment, the processor 154 is configured to be implanted in any place, as desired.

According to one embodiment, illustrated in FIG. 10, the processor 154 is configured to be implanted in the vicinity of the ear drum 950 aside the cochlea 920. According to another embodiment, the processor 154 is configured to be implanted in the middle ear in the vicinity of the cochlea 920, aside the cochlear receiving antenna 152.

Figure 11:
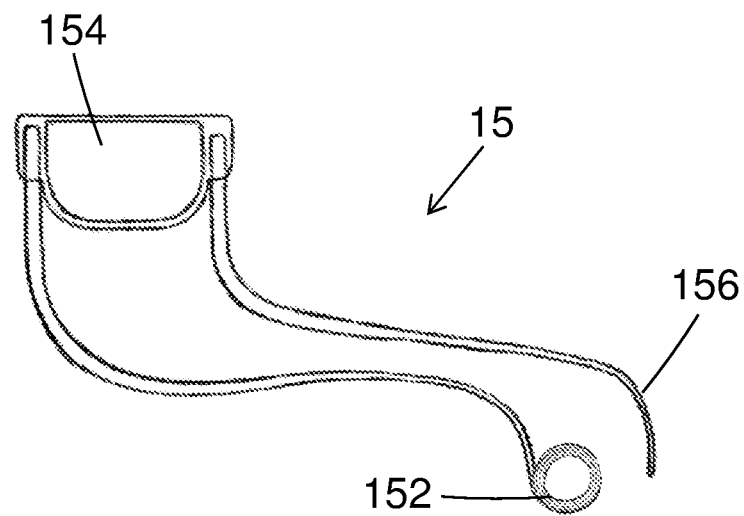
FIG. 11 schematically illustrates, according to an exemplary embodiment of the present subject matter, a perspective view of an implanted unit comprising a processor that is configured to be implanted under the skin, in the vicinity of the pinna, on the mastoid bone.

Referring now to FIG. 11 schematically illustrating, according to an exemplary embodiment of the present subject matter, a perspective view of an implanted unit comprising a processor that is configured to be implanted under the skin, in the vicinity of the pinna, on the mastoid bone.

Figure 12:
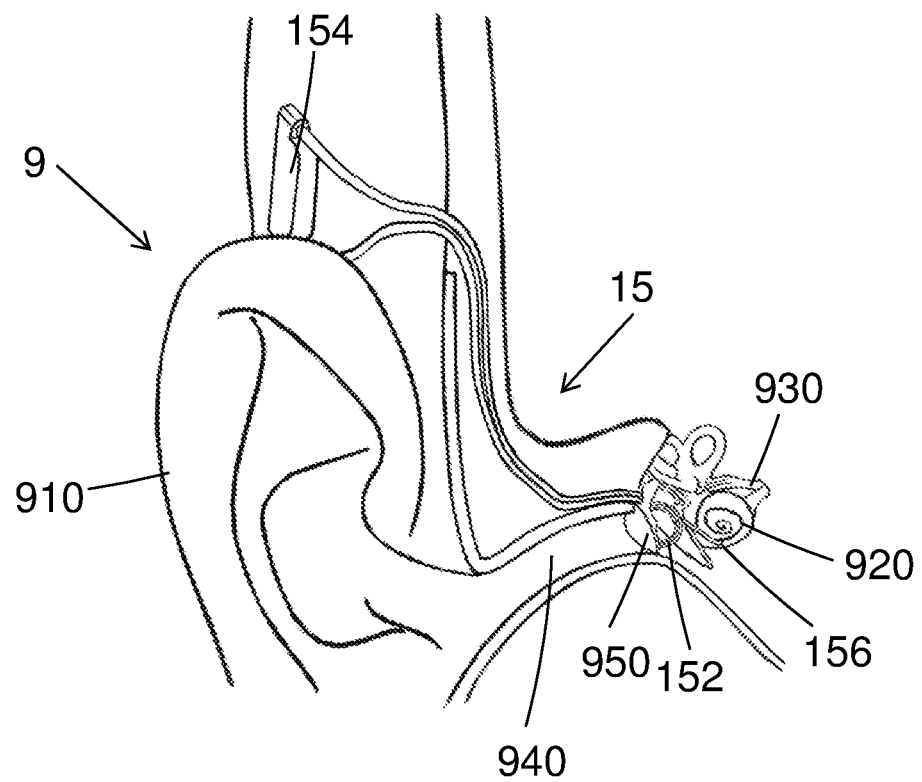
FIG. 12 schematically illustrates, according to an exemplary embodiment of the present subject matter, a perspective view of internal components of a human ear and an implanted unit implanted in the vicinity of the cochlea, the implanted unit comprising a processor that is configured to be implanted under the skin, in the vicinity of the pinna, on the mastoid bone.

Referring now to FIG. 12 schematically illustrating, according to an exemplary embodiment of the present subject matter, a perspective view of internal components of a human ear and an implanted unit at least partially implanted in the vicinity of the cochlea, the implanted unit comprising a processor that is configured to be implanted under the skin, in the vicinity of the pinna, on the mastoid bone.

According to one embodiment, illustrated in FIGS. 11 and 12, the processor 154 is configured to be implanted under the skin, in the vicinity of the pinna 910, on the mastoid bone. This embodiment is preferred for at least two reasons. Firstly, the surgical procedure of implanting a processor under the skin, in the vicinity of the pinna 910, on mastoid bone, and usage of such a processor are currently known in the art. This ensures that the hidden cochlear implant system 1 of the present subject matter would function properly, since according to this embodiment it employs a processor and surgical procedure that are already known and reliable. Another advantage is that the components of the hidden cochlear implant system 1 are hidden, and therefore not recognizable.

According to one embodiment, the electrode array 156 is configured to receive electrical sound signals from the processor 154, and stimulate the auditory nerve 930 with these electrical sound signals. According to another embodiment, the electrode array 156 is configured to be in contact with the auditory nerve 930. Any type of electrode array 156 known in the art, that is configured to stimulate the auditory nerve 930 with electrical sound signals, is under the scope of the present subject matter, for example an electrode configured to transmit electrical pulses, a vibrating electrode configured to stimulate the auditory nerve 930 by vibrations, and the like.

Figure 13:
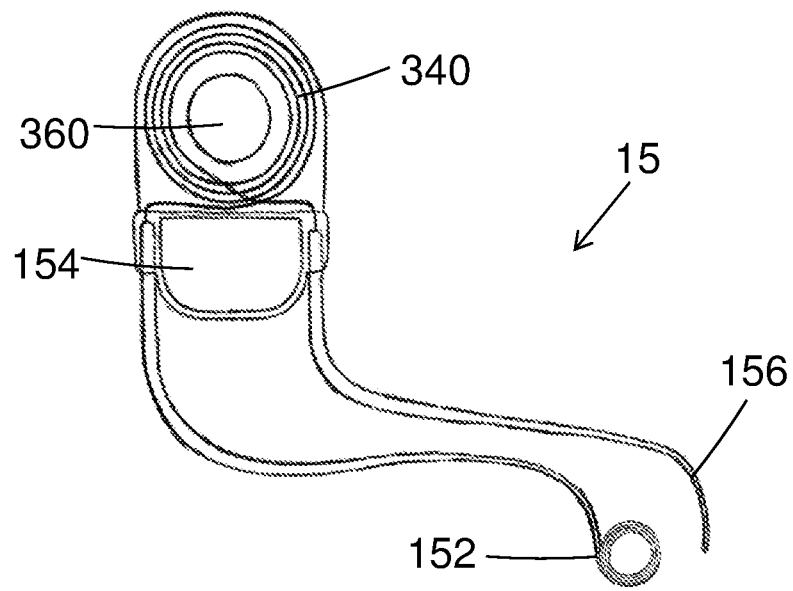
FIG. 13 schematically illustrates, according to an exemplary embodiment of the present subject matter, a side view of another embodiment of an implanted unit of a hidden cochlear implant system.

Referring now to FIG. 13 schematically illustrating, according to an exemplary embodiment of the present subject matter, a side view of another embodiment of an implanted unit of a hidden cochlear implant system.

Referring now to FIG. 14 schematically illustrating, according to an exemplary embodiment of the present subject matter, a perspective view of internal components of a human ear and another embodiment of an implanted unit that is implanted partially in the vicinity of the cochlea, and partially implanted under the skin, in the vicinity of the pinna, on the mastoid bone.

As mentioned above, according to one embodiment, the implanted unit 15 is configured to receive electrical energy, for example in a form of a wireless carrier signal, and data, for example in a form of a modulated wireless carrier signal, from the canal unit 10, and eventually stimulate the auditory nerve 930 with electrical sound signals as described above, given that the wireless carrier signal is modulated. According to another embodiment, the implanted unit 15 is further configured to receive electrical energy, for example in a form of a wireless carrier signal, and data, for example in a form of a modulated wireless carrier signal from an external source such as transmitting antenna 330 of a prior art cochlear device 3, and eventually stimulate the auditory nerve 930 with electrical sound signals as described above.

According to one embodiment, the implanted unit 15 that is configured to receive electrical energy and data from the canal unit 10 and from source such as the external transmitting antenna 330 can be implanted in a user that has not been using any type of cochlear implant before.

One advantage of the implanted unit 15 that is configured to receive electrical energy, for example in a form of a wireless carrier signal from the canal unit 10 and from the external transmitting antenna 330 is that it allows a user to switch between usage of a canal unit 10 and between an external microphone 310, an external modulator 320, and an external transmitting antenna 330. Thus, for example when a user cannot use the canal unit 10, for example because of an ailment in the ear canal 940, the user can still be able to hear sound and speech by using the external microphone 310, the external modulator 320, and the external transmitting antenna 330. Another advantage of the implanted unit 15 that is configured to receive electrical power and data from the canal unit 10 and from the external transmitting antenna 330 is that the implanted unit 15 that is configured to receive electrical power and data from the canal unit 10 and from the external transmitting antenna 330 allows switching to a hidden cochlear implant system 1 of the present subject matter, without a need to remove components of the prior art cochlear implant 3.

It should be noted that the functions of the components of the implanted unit 15 that is configured to receive electrical energy from the canal unit 10 and from the external transmitting antenna 330 and the interrelations of the components of the implanted unit 15 that is configured to receive also a wireless carrier signal from the canal unit 10 and from the external transmitting antenna 330, as well as their positions in the ear 9 and in the vicinity of the ear 9, are similar to those described above. Therefore, only a brief description of the implanted unit 15 that is configured to receive electrical energy and data from the canal unit 10 and from the external transmitting antenna 330 would be given hereinafter, in combination with FIGS. 13 and 14.

According to one embodiment, the implanted unit 15 that is configured to receive electrical energy and data from the canal unit 10 and from the external transmitting antenna 330 comprises a cochlear receiving antenna 152 that is preferably placed in the middle ear, an internal receiving antenna 340 that is preferably placed in proximity of the mastoid bone, a processor 154, and an electrode array 156. The cochlear receiving antenna 152 is electrically connected to the processor 154, the internal receiving antenna 340 is electrically connected to the processor 154, and the processor 154 is electrically connected to the electrode array 156. According to another embodiment, the implanted unit 15 that is configured to receive electrical energy and data from the canal unit 10 and from the external transmitting antenna 330 can further comprise an internal magnet 360.

As described above, the canal transmitting antenna 108 is configured to transmit electrical energy and data, and the cochlear receiving antenna 152 is configured to receive the electrical energy and data. Any type of wireless communication, as well as transmission of electrical energy and data, between the canal transmitting antenna 108 and the cochlear receiving antenna 152 is under the scope of the present subject matter. For example, usage of electromagnetic radio signals, and usage of short-wavelength ultra-high frequency (UHF) radio waves—a technology known as "Bluetooth". Another example is usage of optical energy transmission. According to this example, the canal transmitting antenna 108 is of a type of an optical transmitter 109, as illustrated in FIG. 6, for example an optical transmitter in a form of a LED, and the cochlear receiving antenna 152 is of a type of an optical receiver 153, as illustrated in FIG. 15, for example in a form of a photoelectric cell.

Referring now to FIG. 15 schematically illustrating, according to an exemplary embodiment of the present subject matter, a perspective see-through view of a side view of an implanted unit of a hidden cochlear implant system, further comprising a cochlear optical receiver instead of the cochlear receiving antenna.

Even not shown, it should be noted that the cochlear optical receiver 153 can replace also the cochlear receiving antenna 152 of the implanted unit 15 that is illustrated, for example, in FIG. 9.

Referring now to FIG. 16 schematically illustrating, according to an exemplary embodiment of the present subject matter, a perspective view of internal components of a human ear and an implanted unit implanted partially in the vicinity of the cochlea, and partially implanted under the skin, in the vicinity of the pinna, on the mastoid bone, as well as a canal unit inserted in the ear canal.

FIG. 16 illustrates a human ear 9, where an implanted unit is implanted according to embodiments described above, and a canal unit 10 is inserted in the ear canal 940 according to embodiments described above. This embodiment is advantageous, as described above, since it allows a user to use either the canal unit 10, or the external components of the prior art cochlear implant 3.

Referring now to FIG. 17 schematically illustrating, according to an exemplary embodiment of the present subject matter, a side view of an internal receiving antenna adaptor electrically connected to a cochlear receiving antenna.

According to one embodiment, the internal receiving antenna adaptor 172 is configured to be connected to the internal receiving antenna 340. Thus, according to a preferred embodiment, the shape of the internal receiving antenna adaptor 172 is similar to the shape of the internal receiving antenna 340, for example a coil-like structure, as shown in FIG. 17, when the internal receiving antenna 340 has a coil like structure. According to another embodiment, the internal receiving antenna adaptor 172 is electrically connected to the cochlear receiving antenna 152. According to yet another embodiment, the internal receiving antenna adaptor 172 is configured to receive electrical energy and data from the cochlear receiving antenna 152 and transmit electrical energy and data to the internal receiving antenna 340, that is connected to the internal receiving antenna adaptor 172. This embodiment is useful for a user that has already a prior art cochlear implant 3, and desires to use a canal unit 10 instead of the external components of the prior art cochlear implant 3. Thus, the internal receiving antenna adaptor 172 that is electrically connected to a cochlear receiving antenna 152, as illustrated in FIG. 17, is implanted in the user's ear, in a manner that the cochlear receiving antenna 152 is implanted in the middle ear in the vicinity of the cochlea 920 aside the ear drum 950, as shown for example in FIG. 10, while the internal receiving antenna adaptor 172 is connected to the internal receiving antenna 340. Thus, after inserting the canal unit 10 into the ear canal 940, electrical energy and data are received by the cochlear receiving antenna 152, transmitted to the internal receiving antenna adaptor 172, and from there to the internal receiving antenna 340. Then the electrical energy and data4 continue their path as described in relation to the prior art cochlear implant 3.

According to some embodiments, the canal unit 10 is configured to be inserted into the ear canal 940 until the inward side 1024 of the canal unit 10 is in close vicinity to the ear drum 950, more particularly, until the canal transmitting antenna 108, that resides at the inward side 1024 of the canal unit 10, is in close vicinity to the ear drum 950. According to another embodiment, the canal unit 10 is configured to be inserted into the ear canal 940 until the canal transmitting antenna 108 is in an optimal distance from the cochlear receiving antenna 152 that resides in the middle ear on the other side of the ear drum 950. This embodiment is of importance during the process of insertion of the canal unit 10 into the ear canal 940 of a user, because in one hand it is necessary to avoid damage to the ear drum 950 when, for example, the canal unit 10 is inserted too deep into the ear canal 940; and on the other hand it is necessary that the distance between the canal transmitting antenna 108 and the cochlear receiving antenna 152 is optimal, in order get an optimal transmission of signals between the two antennae.

Thus, according to one embodiment, the hidden cochlear implant system 1 is configured to determine the distance between the canal transmitting antenna 108 and the cochlear receiving antenna 152. According to another embodiment, the hidden cochlear implant system 1 is configured to produce an alarm signal when the distance between the canal transmitting antenna 108 and the cochlear receiving antenna 152 reaches a predetermined value. Alternatively, according to yet another embodiment, the hidden cochlear implant system 1 is configured to produce an alarm signal as long as the distance between the canal transmitting antenna 108 and the cochlear receiving antenna 152 is not similar to a predetermined value.

Any method known in the art for determining a distance between a transmitting antenna and a receiving antenna is under the scope of the present subject matter.

One example is transmission of short pulses by the canal transmitting antenna 108, and measurement of the rate of decay of the pulses received by the cochlear receiving antenna 152. As the distance between the canal transmitting antenna 108 and the cochlear receiving antenna 152 is shorter, the rate of decay of the pulses is higher. Thus, a correlation between the decay rate and the distance between the two antennae can be determined or calculated, and used for determining the distance between the antennae, for example during insertion of the canal unit 10 into the ear canal 940.

Another example is letting the canal transmitting antenna 108 to transmit signals in various different frequencies, and determine the frequency that produces the highest voltage in the cochlear receiving antenna 152. This frequency producing the highest voltage is the common resonance frequency of the two antennae. The common resonance frequency depends on the distance between the two antennae. Thus, a correlation between the resonance frequency and the distance between the two antennae can be determined, and used for determining the distance between the antennae, for example during insertion of the canal unit 10 into the ear canal 940.

It should be noted, though, that the aforementioned examples for determining the distance between the canal transmitting antenna 108 and the cochlear receiving antenna 152 should not be considered as limiting the scope of the present subject matter, and that any method for determining the distance between the two antennae is under the scope of the present subject matter.

In addition, any mechanism known in the art for producing an alarm signal according to the aforementioned embodiments, is under the scope of the present subject matter. For example, the hidden cochlear device 1 is configured to produce a sound alarm; a vibration alarm; a light alarm; a wireless alarm that includes transmission of a signal to a computing member, like a computer, a smartphone and the like, when the signal provokes the computing device to produce an alarm; and the like. Accordingly, the hidden cochlear device 1 further comprises at least one alarm signal producer known in the art, as should be understood by a person skilled in the art.

Referring now to FIGS. 18-20 schematically illustrating exemplary embodiments according to the present subject matter of a storing member.

The present subject matter further provides a storing member 5. According to one embodiment, the storing member 5 is configured to store at least one canal unit 10. According to another embodiment, the storing member 5 is configured to protect at least one canal unit 10 that is stored in the storing member 5, against physical impacts, dirt and the like. According to yet another embodiment, the storing member 5 is configured to charge the canal electrical power source 110 of the at least one canal unit 10 that is stored in the storing member 5, given that the canal electrical power source 110 is rechargeable.

According to one embodiment, illustrated for example in FIG. 18, the storing member 5 comprises a base 502 configured to accommodate at least one canal unit 10, and a case 504 configured to accommodate the base 502. According to another embodiment, the storing member 5 further comprises a cover 506 configured to cover the case 504, prevent accidental exit or removal of the at least one canal unit 10, or of the base 502 from the case 504, and in addition prevent entrance of dirt into the case 504 and cause damage to the at least one canal unit 10.

According to one embodiment, the base 502 comprises at least one niche 5022, each niche 5022 configured to accommodate a canal unit 10. According to another embodiment, each niche 5022 is configured to tightly grasp the canal unit 10, in order to avoid accidental release, or falling, of the canal unit 10 from the niche 5022.

According to one embodiment, the base 502 further comprises a handle 5024 configured to be grasped by a user, in order to facilitate insertion of the base 502 into the case 504, removal of the base 502 from the case 504, and carrying the base 502.

According to one embodiment, illustrated in FIGS. 19-20, the storing member 5 further comprises an electricity charging element 508 configured to charge the canal electrical power source 110 of the at least one canal unit 10 that is stored in the storing member 5, given that the canal electrical power source 110 is rechargeable. Any type of electricity charging element 508 known in the art is under the scope pf the present subject matter. Two exemplary embodiments of the electrical charging element 508 are illustrated in FIGS. 19-20.

According to one embodiment, illustrated in FIG. 19, the electricity charging element 508 comprises multiple electrical wires 5082 surrounding the base 502, and the at least one canal unit 10 accommodate on the base 502. The multiple electrical wires 5082 are connected to an electrical power source, for example a mains electricity (not shown), as can be easily understood by a person skilled in the art. Electric power is transferred by electrical induction from the multiple electrical wires 5082, through a metal coil in the canal unit 10, to the canal electrical power source 110. An exemplary metal coil can be the canal transmitting antenna 108 of the canal unit 10, having a coil-like structure.

According to another embodiment, illustrated in FIG. 20, the electricity charging element 508 comprises multiple electrical wires 5084 positioned on a bottom of each niche 5022 of the base 502. A canal unit 10 is placed in a niche 5022 when the canal transmitting antenna 108 faces the bottom of the niche 5022 and the multiple electrical wires 5084. The multiple electrical wires 5084 are connected to an electrical power source, for example a mains electricity (not shown), as can be easily understood by a person skilled in the art. Electric power is transferred by electrical induction from the multiple electrical wires 5084, through the canal transmitting antenna 108, given that the canal transmitting antenna 108 has a coil-like structure, to the canal electrical power source 110.

Figure 21:
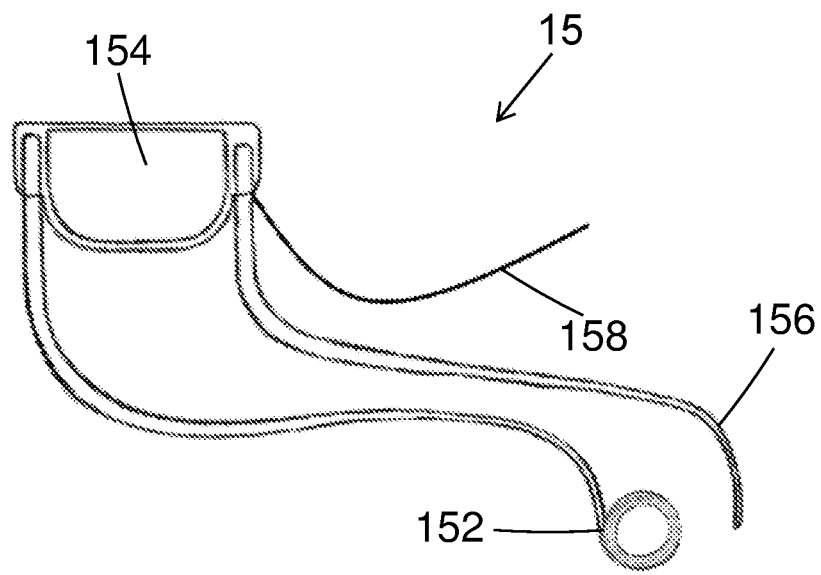
FIG. 21 schematically illustrates, according to an exemplary of the present subject matter, a side view of another embodiment of an implanted unit of a hidden cochlear implant system further comprising a ground.

Referring now to FIG. 21, schematically illustrating, according to an exemplary of the present subject matter, a side view of another embodiment of an implanted unit of a hidden cochlear implant system further comprising a ground.

According to one embodiment, the implanted unit 15 further comprises a ground 158, configured to prevent damage to the brain in case of a short circuit, as known in the art. The other components illustrated in FIG. 21 are similar to the components shown in FIG. 11.

Figure 22:
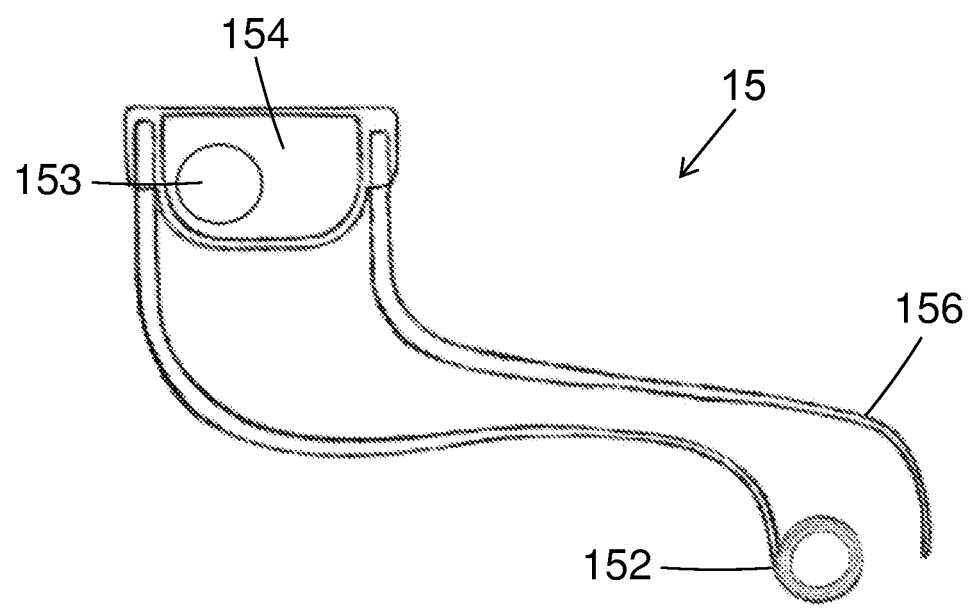
FIG. 22 schematically illustrates, according to an exemplary of the present subject matter, a side view of another embodiment of an implanted unit of a hidden cochlear implant system further comprising an implant electrical power source.

Referring now to FIG. 22 schematically illustrating, according to an exemplary of the present subject matter, a side view of another embodiment of an implanted unit of a hidden cochlear implant system further comprising an implant electrical power source.

According to one embodiment, the implanted unit 15 further comprises an implant electrical power source 153. Any type of electrical power source known in the art can serve as an implant electrical power source 153. For example, the implant electrical power source 153 can be a battery, a rechargeable battery, and the like. According to another embodiment, the implant electrical power source 153 is electrically connected to any component of the implanted unit 15 that requires supply of electrical power, for example the processor 154, and the like. The other components illustrated in FIG. 21 are similar to the components shown in FIG. 11.

Figure 23A:
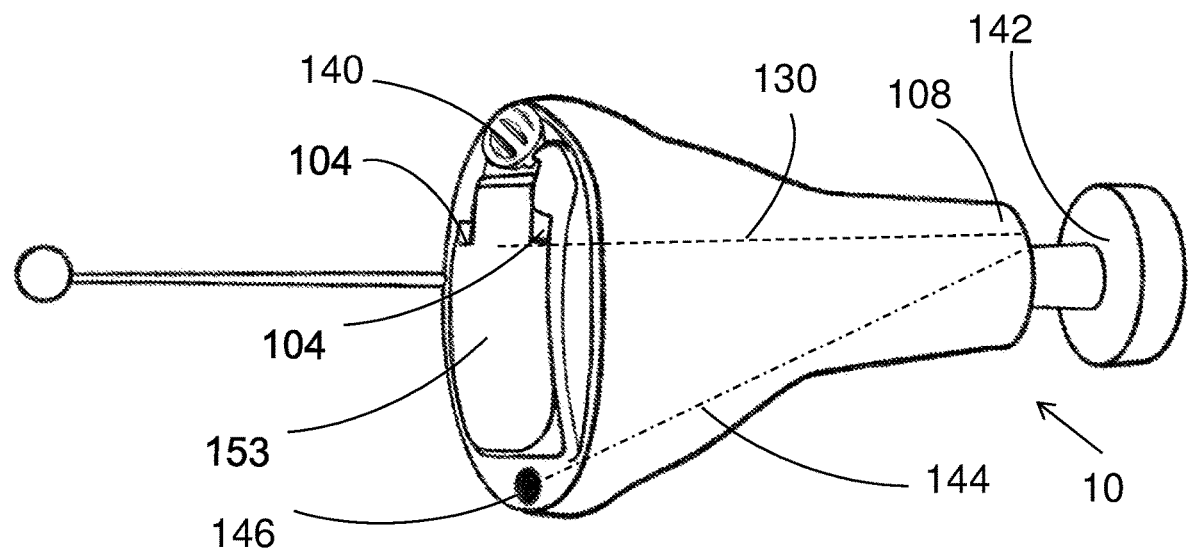
FIG. 23A schematically illustrates, according to an embodiment of the present subject matter, a view of a canal unit of the hidden cochlear implant system.

Referring now to FIG. 23A schematically illustrating, according to an embodiment of the present subject matter, a view of a canal unit of the hidden cochlear implant system. The hidden cochlear implant system comprises a canal unit 10 that allows adjustment of a distance between the canal transmitting antenna 108 and a receiving antenna (not shown in this figure). For example, in order to personalize the hidden cochlear implant system to dimensions of the ear of individual users. For example, the canal processor 107 (not shown in FIG. 23A) is configured to determine the distance between the canal transmitting antenna 108 and the receiving antenna (such as receiving antenna 152 shown as example in FIGS. 10 and 16) using a software that calculates the distance between the canal transmitting antenna 108 and the receiving antenna according to a difference between the level of energy that is transmitted from the canal transmitting antenna 108 and the level of energy received by the receiving antenna. According to the amount of energy gap, the software calculates how much energy is absorbed by the receiving antenna 152 and translates this value into the distance between the canal transmitting antenna 108 and the receiving antenna. According to the output of the software, the distance between the canal transmitting antenna 108 and the receiving antenna can be adjusted in order to optimize the transfer of energy from the canal transmitting antenna 108 to the receiving antenna.

According to one embodiment, the hidden cochlear implant system is configured to adjust the distance between the canal transmitting antenna 108 and the receiving antenna (152, as an example). According to an exemplary embodiment, the canal unit 10 comprises a distance adjuster 130 (shown in dash line since it is preferably an internal mechanism) that is configured to change a position of the transmitting antenna 108, preferably by pulling and pushing in the canal unit 10, thereby adjusting the distance between the canal transmitting antenna 108 and the receiving antenna.

An exemplary distance adjuster 130 is a screw 130, as shown in FIG. 23A that is connected to the transmitting antenna 108 at one side of the screw. Screwing the screw 130, for example with a corresponding screwdriver, changes the position of the transmitting antenna 108 in the canal unit 10. For this purpose, a head 140 of the screw 130 is positioned on a side of the canal unit 10 that is directed towards the outer side of the ear canal 940 in order to allow access to the screw 130 with a screwdriver. Another exemplary distance adjuster 130 is a motor for example an electric motor that is configured to change the position of the transmitting antenna 108 in the canal unit 10 as described above.

According to an additional embodiment, canal unit 10 comprises a ventilation channel 144 (shown by a dash line). The ventilation channel 144 communicates the interior part of the ear with the exterior part. Canal unit 10 can reside inside user's ear canal for a long time, and in order to allow air to flow into the canal space, a hollow channel can be used. Optionally, hollow channel that is part of the ventilation channel 144 is in the same perimeter as the canal unit 10. The ventilation channel 144 starts at the interior side 146 of canal unit 10 and reaches the external end thus allowing passage of air. The ventilation canal 144 can be located in several locations along the canal unit 10, for example, having the ventilation channel 144 at the lower end of the canal unit fits the style of a completely in canal (CIC) processor. The ventilation channel can also comprise filters, wax blocker, valves and other parts.

Figure 23B:
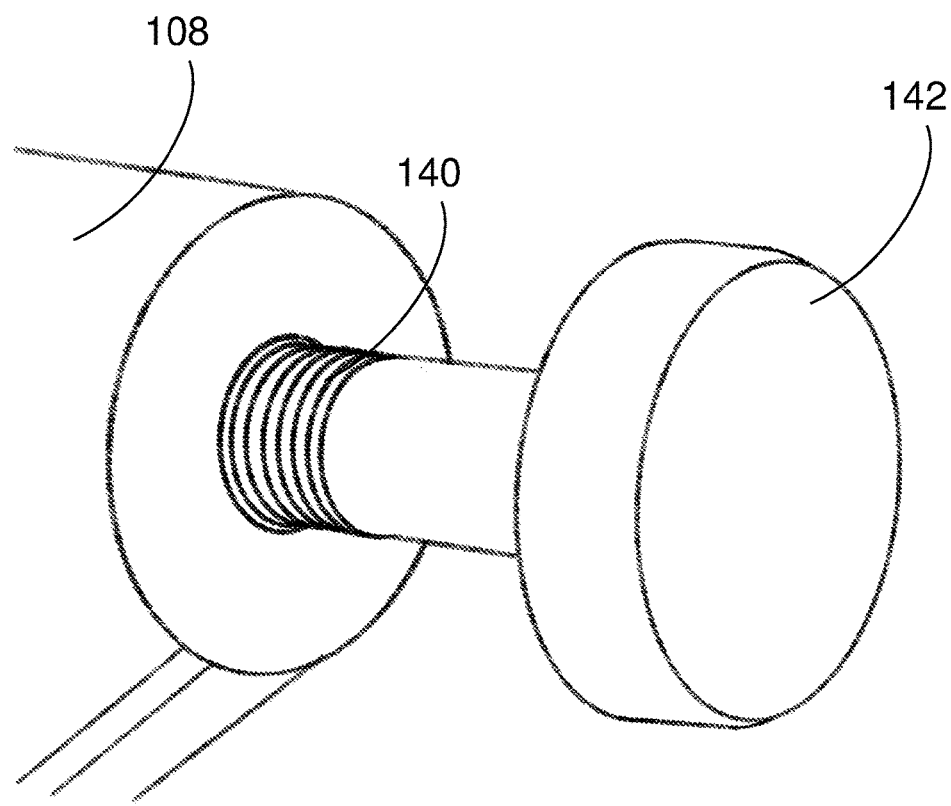
FIG. 23B schematically illustrates, according to another embodiment of the present subject matter, a partial view of a canal unit of the hidden cochlear implant system.

Referring now to FIG. 23B schematically illustrating, according to an embodiment of the present subject matter, a partial view of a canal unit of a hidden cochlear implant system. According to one embodiment, the hidden cochlear implant system is configured to adjust the distance between the canal transmitting antenna 108 and the receiving antenna 152. Adjusting mechanism 140 is configured to change the distance between the canal transmitting antenna 108 and the receiving antenna 152. According to this embodiment, the canal transmitting antenna 108 is attached to a moving part 142 that is capable of moving towards the receiving antenna 152. Moving part 142 comprises a screw having a thread like end that comprises a tapering groove that spirals towards or away from the receiving antenna (not shown in this figure).

Figure 24:
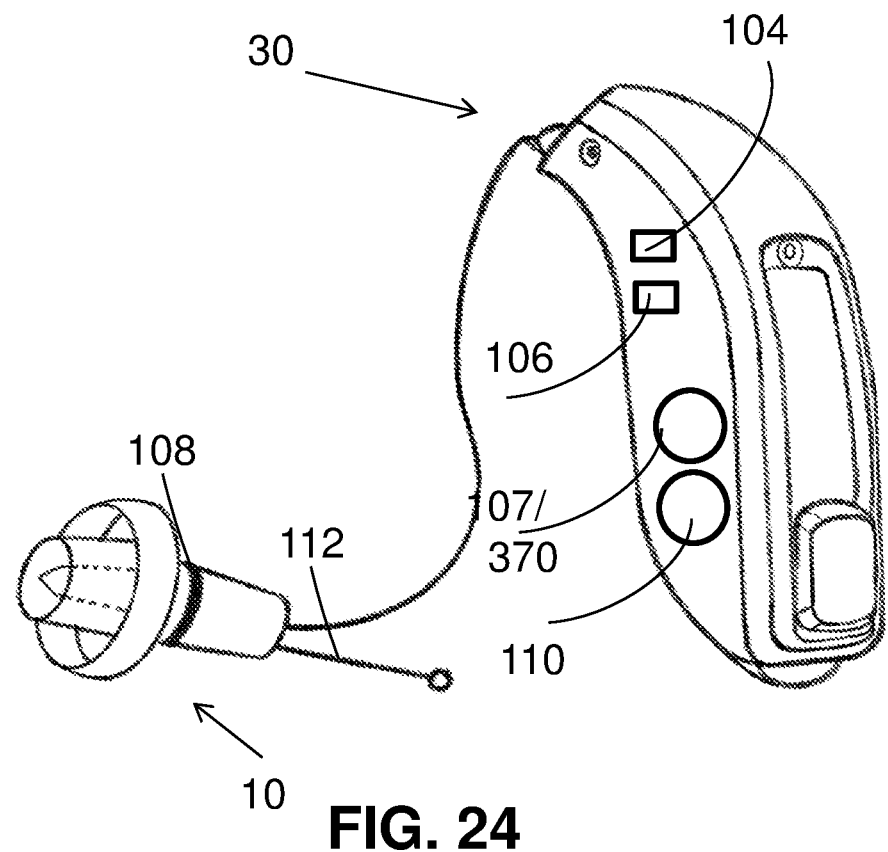
FIG. 24 schematically illustrates, according to another embodiment of the present subject matter, an implant system that some of the implant system components are configured to reside in an external unit.

Referring now to FIG. 24 schematically illustrating, according to an embodiment of the present subject matter, an implant system in which some of the implant system components are configured to reside in an external unit. According to the embodiments described above, the canal unit 10 comprises all the components of the canal unit described above, meaning that all these components reside in the ear canal 940. According to some other embodiments, some of these components can reside in an external unit 30 except of the transmitting antenna 108 and in some embodiments the grasping element 112 that must reside in the ear canal 940. For example, each of the microphones 104, modulator 106, processor 370, electric power source 110 can reside in an external unit 30. Each of the other components can reside either in the canal unit 10 or in the external unit 30. The components that reside in the external unit are electrically connected to the components that reside in the canal unit 10, for example, wirily or wirelessly.

The external unit 30 is configured to be positioned externally to the ear. Preferably, the external unit 30 is placed behind the ear. For example, to the pinna or to any item convenient to a user. An advantage of this embodiment is related, for example, to the electrical power source. Placing the electrical power source in the external unit 30 allows usage of a larger electrical power source having a longer battery life and a larger electrical capacity than in a case in which the electrical power source is implanted.

Figure 25:
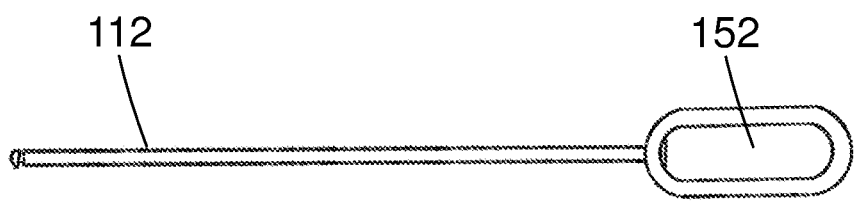
FIG. 25 schematically illustrates, according to an embodiment of the present subject matter, a view of a receiving antenna.

Referring now to FIG. 25 schematically illustrating, according to an embodiment of the present subject matter, a view of a receiving antenna. According to one embodiment, the receiving antenna 152 is elliptically shaped thus facilitating insertion of the receiving antenna 152 into the middle ear, which resides between the ear drum 950 and the cochlea 920, and can more conveniently being inserted during surgery using the grasping element 112.

Figure 26:
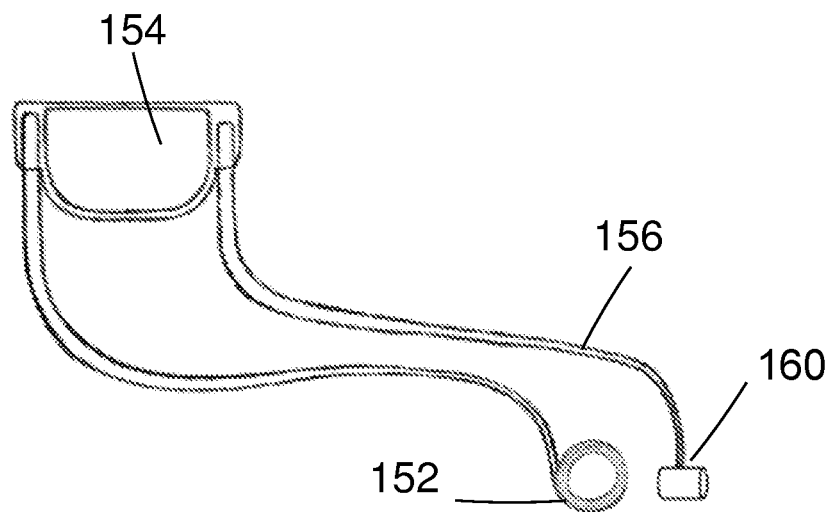
FIG. 26 schematically illustrates, according to an exemplary embodiment of the present subject matter, a perspective view of an implanted unit comprising a processor that is configured to be implanted under the skin, in the vicinity of the pinna, on the mastoid bone FIG. 27 schematically illustrates, according to an embodiment of the present subject matter, a view of an exemplary conduit

Referring now to FIG. 26 schematically illustrates, according to an exemplary embodiment of the present subject matter, a perspective view of an implanted unit comprising a processor that is configured to be implanted under the skin, in the vicinity of the pinna, on the mastoid bone. According to one embodiment, the electrode array 156 is configured to receive electrical sound signals from the processor 154, and stimulate the auditory nerve with these electrical sound signals. According to another embodiment, the electrode array 156 is configured to be in contact with the auditory nerve. Vibrating electrode array 160 is configured to stimulate the auditory nerve by vibrations.

Figure 27:
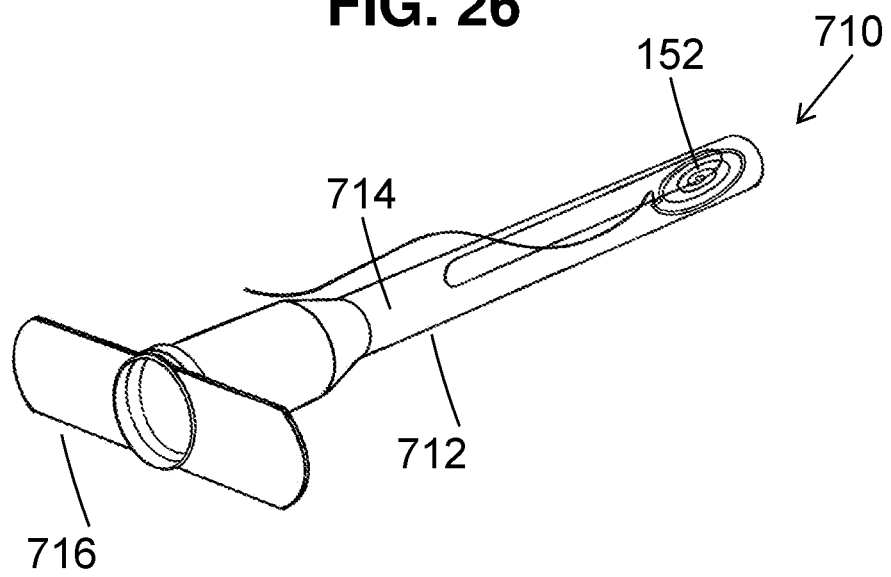

Referring now to FIG. 27 schematically illustrating, according to an embodiment of the present subject matter, a view of an exemplary conduit. According to another embodiment, the hidden cochlear implant system further comprises a conduit 710 configured to facilitate implementation of at least one component as described above of the implanted unit. For example, in order to facilitate implementation of the receiving antenna 152, or the entire implanted unit in the middle ear.

The conduit 710 comprises an elongated hollow element 712 comprising a lumen 714, and a pushing element 716 configured to be inserted into the lumen 714 of the elongated hollow element 712 and push at least one component of the implanted unit (such as implanted unit 15, as shown in FIG. 9 as an example) placed in the lumen 714. For implanting the implanted element in the middle ear, at least one component of the implanted unit, for example the receiving antenna 152, is placed inside the lumen 714 of the elongated hollow element 712. Then, the elongated hollow element 712 is brought to the vicinity of the middle ear and the at least one component of the implanted unit is pushed into the middle ear using the pushing element 716.

According to one embedment the receiving antenna 152 is configured to be inserted into the lumen 714 of the elongated hollow element 712, and pushed out of the elongated hollow element 712 into the middle ear during implementation. According to another embodiment, the size and shape of the receiving antenna 152 facilitates insertion of the receiving antenna into the lumen 714. According to yet another embodiment, the receiving antenna 152 is made of a material having a shape memory, for example silicone, namely during insertion of the receiving antenna 152 into the lumen 714, the size and shape of the receiving antenna 152 is adapted to the dimensions of the lumen 714, and after implanting, the receiving antenna 152 in the middle ear, the receiving antenna 152 assumes its original size and shape.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

I claim:

1. A hidden cochlear implant system for an ear, comprising:
   a canal unit; and
   an implanted unit,
   wherein the canal unit comprises:
   at least one canal microphone configured to receive sound signals and convert the sound signals to electrical sound signals;
   a canal transmitting antenna configured to transmit electrical energy, wherein the electrical energy comprises power and the electrical sound signals that comprise data to the implanted unit; and
   a canal electrical power source,
   wherein the at least one canal microphone is electrically connected to the canal transmitting antenna, and the canal electrical power source is electrically connected to any component of the canal unit that requires supply of electrical power, and
   wherein the implanted unit comprises:
   a cochlear receiving antenna configured to be implanted in the ear and receive the electrical energy transmitted by the canal transmitting antenna;
   a processor configured to receive data as well as power from the cochlear receiving antenna and transmit electrical signals as electrical pulses to a cochlea; and
   an electrode array configured to be implanted in the cochlea,
   wherein the cochlear receiving antenna is electrically connected to the processor, and the processor is electrically connected to the electrode array, and wherein the processor and the electrode array of the implanted unit receive power solely from the canal transmitting antenna and through the cochlear receiving antenna.

2. The hidden cochlear implant system according to claim 1, wherein the processor is configured to be implanted under a skin on a mastoid bone.

3. The hidden cochlear implant system according to claim 1, wherein the cochlear receiving antenna has a coil-like structure and is configured to receive the electrical energy electromagnetically and wherein the canal transmitting antenna has a coil-like structure and is configured to transmit the electrical energy electromagnetically.

4. The hidden cochlear implant system according to claim 1, wherein data communication between the external antenna and the internal antenna is wireless.

5. The hidden cochlear implant system according to claim 1, wherein the processor is configured to be implanted aside the cochlea.

6. The hidden cochlear implant system according to claim 1, wherein the canal transmitting antenna is of a type of an optical transmitter, and the cochlear receiving antenna is of a type of optical receiver, wherein the optical transmitter transfers light energy to the optical receiver and the optical receiver converts light energy into electrical energy and wherein the electrical energy and data are optically transmitted between the canal transmitting antenna and the cochlear receiving antenna.

7. The hidden cochlear implant system according to claim 1, wherein the canal unit further comprises a canal processor, wherein the at least one canal microphone is electrically connected to the canal processor, and the canal processor is electrically connected to the canal modulator, and wherein the canal processor is configured to receive electrical sound signals from the at least one canal microphone, process the electrical sound signals to produce processed electrical sound signals, and transmit the processed electrical sound signals to the canal modulator.

8. The hidden cochlear implant system according to claim 1, wherein the canal electrical power source is rechargeable.

9. The hidden cochlear implant system according to claim 1, wherein the canal unit is configured to adapt its shape and size to the shape and size of an auditory canal of the ear.

10. The hidden cochlear implant system according to claim 1, wherein the canal unit further comprises at least one grasping element configured to facilitate grasping of the canal unit.

11. The hidden cochlear implant system according to claim 1, wherein the hidden cochlear implant is configured to determine a distance between the canal transmitting antenna and the cochlear receiving antenna, and wherein the distance between the canal transmitting antenna and the cochlear receiving antenna is calculated according to a difference between the level of energy that is transmitted from the canal transmitting antenna and the level of energy received by the cochlear receiving antenna.

12. The hidden cochlear implant system according to claim 1, wherein the canal unit further comprises an adjusting mechanism configured to change the distance between the canal transmitting antenna and the cochlear receiving antenna.

13. The hidden cochlear implant system according to claim 1, wherein the electrode array is a vibrating electrode array configured to stimulate an auditory nerve of the ear by vibrations.

14. The hidden cochlear implant system according to claim 1, wherein the canal unit further comprises a ventilation channel allowing air to flow into the ear canal.

15. A hidden cochlear implant system for an ear, comprising:
a canal unit comprising:
at least one canal microphone configured to receive sound signals and convert the sound signals to electrical sound signals;
a canal transmitting antenna configured to transmit electrical energy, wherein the electrical energy comprises power and the electrical sound signals that comprise data to the implanted unit; and
a canal electrical power source,
wherein the at least one canal microphone is electrically connected to the canal transmitting antenna, and the canal electrical power source is electrically connected to any component of the canal unit that requires supply of electrical power,
an implanted unit comprising:
a cochlear receiving antenna configured to be implanted in the ear and receive the electrical energy transmitted by the canal transmitting antenna;
a processor configured to receive data as well as power from the cochlear receiving antenna and transmit electrical signals as electrical pulses to a cochlea; and
an electrode array configured to be implanted in the cochlea; and
an additional internal receiving antenna, electrically connected to the processor, wherein the internal receiving antenna is configured to be implanted under a skin on a mastoid bone, and to receive electrical energy that comprises power and the electrical sound signal that comprises data from an external transmitting antenna, wherein the processor and the electrode array of the implanted unit can receive the electrical energy from the canal transmitting antenna through the cochlear receiving antenna and also from the external transmitting antenna through the additional internal receiving antenna,
wherein the cochlear receiving antenna is electrically connected to the processor, and the processor is electrically connected to the electrode array, and wherein the processor and the electrode array of the implanted unit receive power from the canal transmitting antenna and through the cochlear receiving antenna.

16. Wireless transmission of electrical energy in a hidden cochlear implant in an ear comprising:
a transmitting antenna positioned in an ear canal, wherein the transmitting antenna is configured to transmit electrical energy that comprises power; and
an internal receiving antenna configured to be implanted in the ear and receive the power transmitted by the transmitting antenna, wherein the internal receiving antenna receives the power solely from the transmitting antenna in the ear canal, wherein the internal receiving antenna has a coil-like structure and is configured to electromagnetically receive the power and wherein the transmitting antenna has a coil-like structure and is configured to electromagnetically transmit the electrical energy.

17. Wireless transmission of electrical energy according to claim 16, further comprising a power source that can be positioned in the ear canal or externally to the ear.

18. Wireless transmission of electrical energy according to claim 16, wherein the wireless transmission of power between the transmitting antenna and the internal receiving antenna is through electromagnetic radio signals.

19. Wireless transmission of electrical energy according to claim 16, wherein at least one of the transmitting antenna is an optical transmitter, and the internal receiving antenna is an optical receiver, wherein the optical transmitter is transferring light energy to the optical receiver and wherein the optical receiver converts light energy into electrical energy.

20. Wireless transmission of electrical energy according to claim 16, wherein data communication between the external antenna and the internal antenna is wireless.

21. Wireless transmission of electrical energy according to claim 16, wherein a distance between the transmitting antenna and the internal receiving antenna can be calculated from a difference between a level of energy that is transmitted from the transmitting antenna and a level of energy received by the internal receiving antenna.

22. Wireless transmission of electrical energy according to claim 16, wherein the electrical energy further comprises electrical sound signals that comprises data.

* * * * *